(12) United States Patent  (10) Patent No.: US 8,236,959 B2
Kankan et al.  (45) Date of Patent: Aug. 7, 2012

(54) PROCESS FOR PREPARING ISOMERS OF CARMOTEROL

(75) Inventors: Rajendra Narayanrao Kankan, Maharashtra (IN); Dharmaraj Ramachandra Rao, Maharashtra (IN); Dilip Birari, Maharashtra (IN); Ashwini Amol Sawant, Maharashtra (IN)

(73) Assignee: Cipla Limited, Mumbai (IN)

( * ) Notice: Subject to any disclaimer, the term of this patent is extended or adjusted under 35 U.S.C. 154(b) by 181 days.

(21) Appl. No.: 12/528,687

(22) PCT Filed: Feb. 28, 2008

(86) PCT No.: PCT/GB2008/000677
§ 371 (c)(1),
(2), (4) Date: Jan. 20, 2010

(87) PCT Pub. No.: WO2008/104781
PCT Pub. Date: Sep. 4, 2008

(65) Prior Publication Data
US 2010/0113790 A1 May 6, 2010

(30) Foreign Application Priority Data
Feb. 28, 2007 (IN) .......................... 391/MUM/2007

(51) Int. Cl.
*C07D 215/28* (2006.01)
(52) U.S. Cl. ....................................... 546/157
(58) Field of Classification Search .................... 546/157
See application file for complete search history.

(56) References Cited

U.S. PATENT DOCUMENTS

| | | | |
|---|---|---|---|
| 4,579,854 A | 4/1986 | Iwakuma et al. | |
| 4,579,857 A * | 4/1986 | Sherlock | 514/341 |
| 4,894,219 A * | 1/1990 | Baker et al. | 435/7.21 |
| 7,307,076 B2 * | 12/2007 | Konetzki et al. | 514/230.5 |
| 2007/0065366 A1 | 3/2007 | Soliani Raschini et al. | |

FOREIGN PATENT DOCUMENTS

| | | |
|---|---|---|
| JP | 5025045 | 2/1993 |
| WO | 9525104 A1 | 9/1995 |
| WO | 2004076422 A1 | 9/2004 |
| WO | 2005110990 A1 | 11/2005 |
| WO | 2008104781 A1 | 9/2008 |

OTHER PUBLICATIONS

Kobayashi, Yukio, et al., Database CA Online, Chemical Abstracts Service, 1993, 2 pages, Columbus, OH, XP 002480770.
Foreign communication from the priority application—International Search Report and Written Opinion, PCT/GB2008/000677, Jul. 14, 2008, 18 pages.
Foreign communication from the priority application—International Preliminary Report on Patentability, PCT/GB2008/000677, Jul. 31, 2009, 12 pages.
Matsukawa, Masami, et al., "Enzyme-linked immunosorbent assay for TA-2005-glucuronide in human plasma," Journal of Pharmaceutical and Biomedical Analysis, 1998, vol. 17, pp. 245-254, XP-002480769.
Matsumura, Konomu, "The Friedel and Crafts Reaction with 8-Hydroxyquinoline," Journal of the American Chemical Society, 1930, vol. 52, pp. 4433-4436.
Foreign communication from a related counterpart application—European examination report, 08709552.7, Apr. 6, 2010, 5 pages.

* cited by examiner

*Primary Examiner* — D M Seaman
(74) *Attorney, Agent, or Firm* — Conley Rose, P.C.; Rodney B. Carroll

(57) ABSTRACT

A process for preparing a compound of formula (III) comprising condensing an oxiranyl compound of formula (I) with an amine of formula (II) or a salt thereof wherein: $R_1$ is a group selected from alkyl, aryl, allyl, alkoxy, cycloalkyl, heterocyclic, alkenyl, benzocycloalkyl, aralkyl, haloarylalkyl, heteroaralkyl, haloalkyl, alkoxyaralkyl, substituted silyl and benzyl; and $R_2$ is hydrogen, optionally substituted silyl or optionally substituted benzyl.

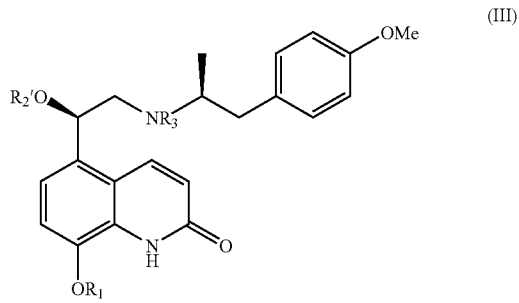

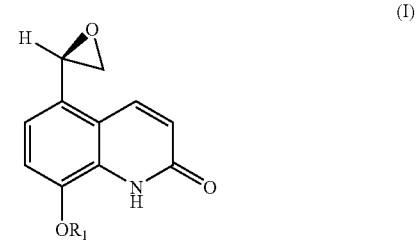

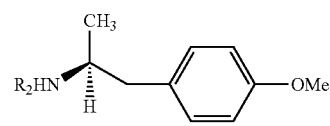

There is also described a process for preparing (R,R)-carmoterol from compound (III).

17 Claims, No Drawings

PROCESS FOR PREPARING ISOMERS OF CARMOTEROL

CROSS-REFERENCE TO RELATED APPLICATIONS

This application is a filing under 35 U.S.C. 371 of International Application No. PCT/GB2008/000677 filed Feb. 28, 2008, entitled "Process for Preparing Isomers of Carmoterol," claiming priority of Indian Patent Application No. 391/MUM/2007 filed Feb. 28, 2007, which applications are incorporated by reference herein in their entirety.

FIELD OF THE INVENTION

The present invention relates to a novel process for the synthesis of R,R-Carmoterol.

BACKGROUND OF THE INVENTION

Carmoterol, chemically termed as 8-hydroxy-5-[1-hydroxy{[2-(4-methoxyphenyl)-1-methylethyl]amino}ethyl]-2(1H)-quinolinone, is a highly potent $\beta_2$-selective adrenoceptor agonist having a long lasting bronchodilating effect. The structure of carmoterol is as shown below:

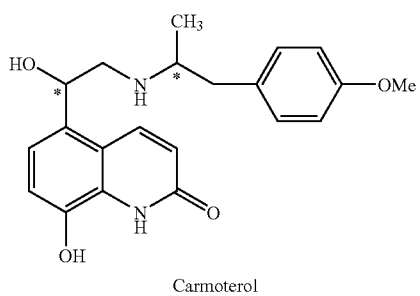

Carmoterol

The asterisks indicate that carmoterol has two chiral centers in the molecule, each of which can exist in two possible configurations (R or S). This gives rise to four possible configurations of carmoterol: (R, R), (S, S), (S, R) and (R, S). Throughout this specification, the first "R" or "S" refers to the configuration of the asymmetric carbon atom at the position of —CH(OH)— and the second "R" or "S" refers to the configuration of the asymmetric carbon atom at the position of —CH(CH₃)—. For example, the term "R,S" refers to the diastereomer of carmoterol wherein the asymmetric carbon atom at the position of —CH(OH)— has the R configuration and the asymmetric carbon atom at the position of —CH(CH₃)— has the S configuration. (R, R) and (S, S) are minor images of each other and are therefore enantiomers. These two enantiomers are referred to as α-isomers. Similarly, (S, R) and (R, S) are an enantiomeric pair and are referred to as β-isomers.

All four isomers of carmoterol have been synthesized and the (R, R) isomer is reported to be the most potent, while the others are less potent.

Carmoterol and its isomers were first disclosed in the U.S. Pat. No. 4,579,854. The process is disclosed in preparation 1 and in examples 2, 3 and 4. The synthetic process employed is depicted in the following Scheme 1.

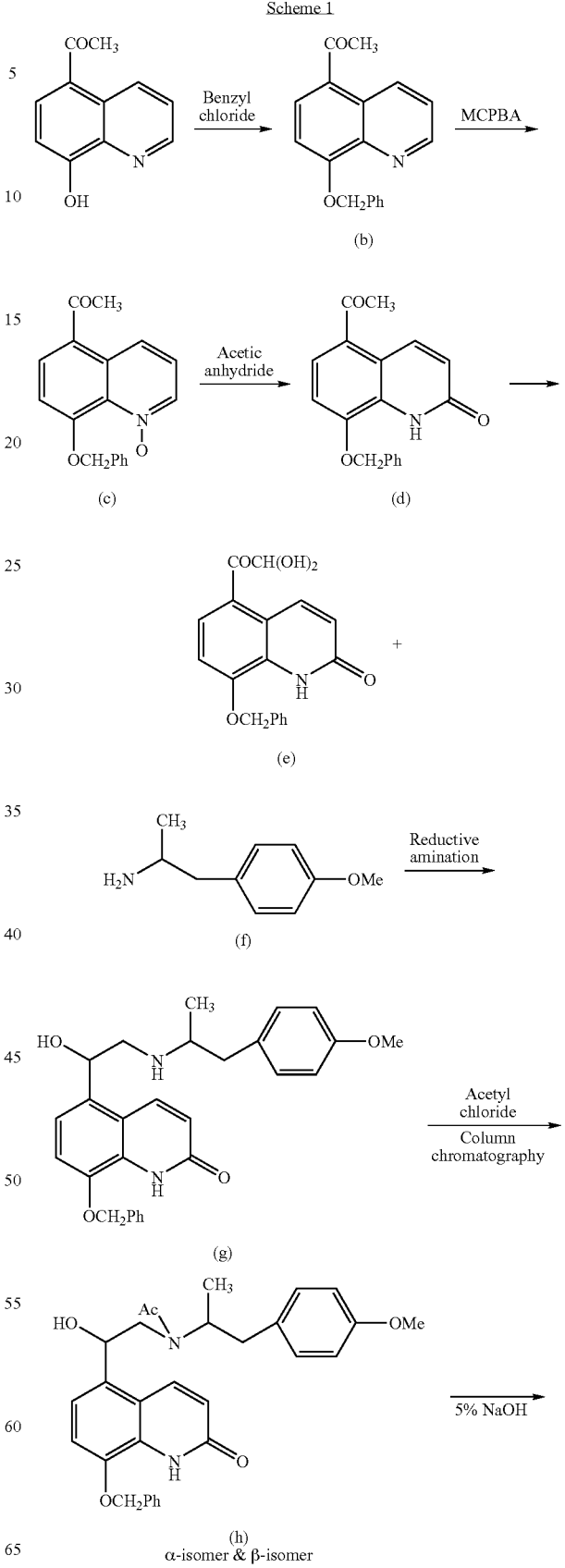

Scheme 1

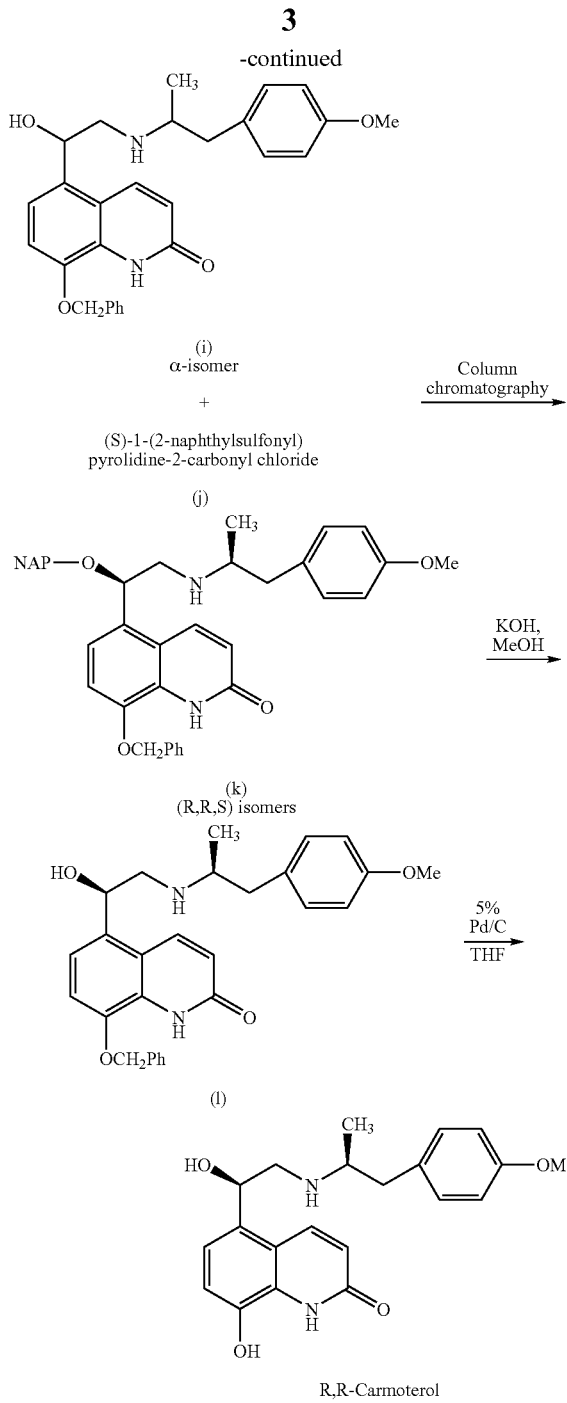

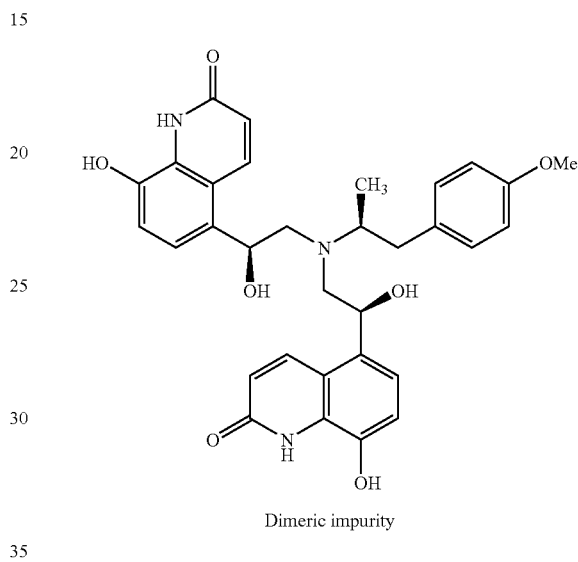

Dimeric impurity

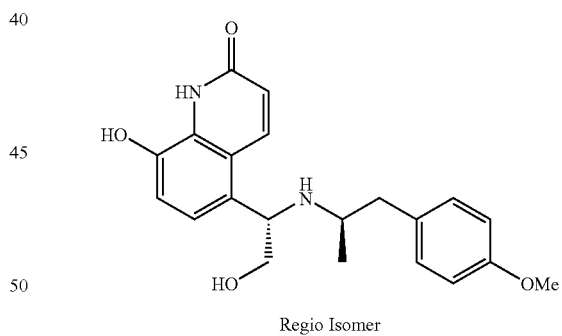

Regio Isomer

A similar process is disclosed in example (5) of U.S. Pat. No. 4,579,854, where compound (e) is reacted with optically pure (R)—N-(2-(p-methoxyphenyl)-1-methylethylamine of compound (f) to give a diastereomeric mixture of carmoterol, which diastereomers are then separated by column chromatography to give the R,R and S,S isomers. These isomers are hydrolysed and reduced to give R, R-carmoterol.

The preparation of optically pure (R)-8-benzyloxy-5-oxiranylcarbostyril was disclosed in WO 95/25104 which involves multisteps for the synthesis and it employs the use of an expensive reagent like benzyltrimethylammonium dichloroiodate. The product is isolated using a tedious process.

WO 95/25104 also relates to a process for preparing (R)-8-benzyloxy-5-oxyranylcarbostyril, an intermediate of carmoterol, and there is no disclosure of a process for preparing carmoterol itself. A compound of formula (III) of WO95/25104 is reacted with the (R)-8-benzyloxy-5-oxiranylcarbostyril compound (II) to form a protected precursor to a carmoterol derivative. The compound (III) is in the form of a free amine. A disadvantage of the process for preparing the carmoterol derivative is that the use of free amine in excess gives rise to dimeric impurities as well as regioisomers which are difficult to separate.

The dimeric impurity of a precursor to carmoterol would have the following structure.

The regiosiomer of carmoterol would have the following structure.

A process for preparing an 8-(substituted oxy)-5-(R)-oxiranylcarbostyril oxiranyl compound is disclosed in patent application, WO 2004/076422. The process involves the use of a halo derivative for preparation of the corresponding halohydrin and cyclisation of the halohydrin to obtain the oxiranyl compound. However, there is no example disclosing the use of any halo compound other than the chloro compound.

WO 2004/076422 also relates to a process for preparing 5-[(R)-2-(5,6-diethyl-indan-2-yl-amino)-1-hydroxy-ethyl]-8-hydroxy-(1H)-quinolin-2-one salt or solvate, and there is no disclosure of a process for preparing carmoterol itself. The compound 2-amino-(5,6-diethyl)-indan is reacted with the 8-(substituted oxy)-5-oxiranylcarbostyril compound to form a protected precursor to the indanyl compound. The 2-amino- (5,6-diethyl)-indan compound is in the form of a free amine. A disadvantage of the process for preparing 5-[(R)-2-(5,6-diethyl-indan-2-yl-amino)-1-hydroxy-ethyl]-8-hydroxy-(1H)-quinolin-2-one salt or solvate is that the use of free amine in excess gives rise to dimeric impurities as well as regioisomers which are difficult to separate.

The processes disclosed in the prior art are cumbersome. Therefore, there exists a need for a more economical and efficient method of making optically pure carmoterol which is suitable for industrial scale up.

The present invention provides a process for synthesis of carmoterol which avoids all the disadvantages associated with prior art.

OBJECTS OF THE INVENTION

The object of the present invention is to provide an improved process for preparing (R,R)-carmoterol and its salts.

Another object of the present invention is to provide novel intermediates for the synthesis of (R,R)-carmoterol.

Yet another object of the present invention is to provide an improved process for preparing the novel intermediates used in the synthesis of (R,R)-carmoterol.

Yet another object of the present invention is to provide a process which is simple, economical and suitable for industrial scale up.

SUMMARY OF THE INVENTION

According to a first aspect of the present invention, there is provided a process for preparing the (R,R)—, (S,S)—, (R,S)— or (S,R)-diastereomer of a compound of formula (III)

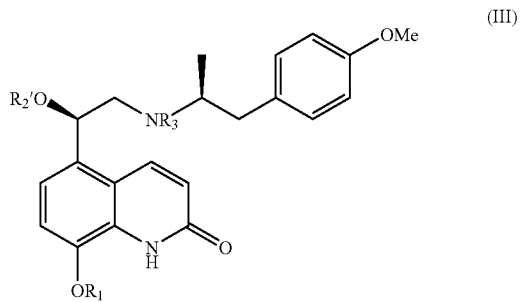

(III)

comprising condensing the R or S enantiomer of an oxiranyl compound of formula (I)

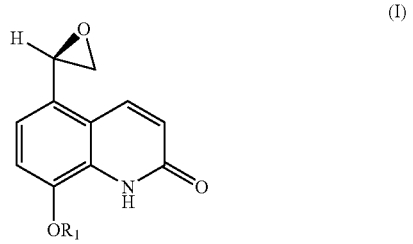

(I)

with the R or S enantiomer of an amine of formula (II) or a salt thereof

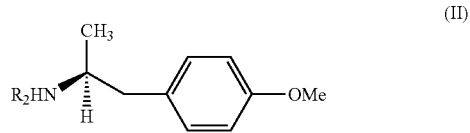

(II)

wherein $R_1$ is a group selected from alkyl, aryl, allyl, alkoxy, cycloalkyl, heterocyclic, alkenyl, benzocycloalkyl, aralkyl, haloarylalkyl, heteroaralkyl, haloalkyl, alkoxyaralkyl, and optionally substituted silyl; $R_2$ is (a) optionally substituted silyl, (b) optionally substituted benzyl or (c) hydrogen; when $R_2$ is optionally substituted silyl, either: $R_2'$ and $R_3$ are the same as $R_2$; $R_2'$ is the same as $R_2$ and $R_3$ is hydrogen; or $R_2'$ is hydrogen and $R_3$ is the same as $R_2$; when $R_2$ is optionally substituted benzyl, $R_2'$ is hydrogen and $R_3$ is the same as $R_2$; and when $R_2$ is hydrogen, $R_2'$ is hydrogen and $R_3$ is hydrogen.

Compound (III) is depicted above in the form of the (R,R)— diastereomer.

In an embodiment, the (R,R)-diastereomer of compound (III) is prepared by reacting the R enantiomer of compound (I) with the R enantiomer of compound (II). Alternatively, the (R,S)-diastereomer of compound (III) is prepared by reacting the R enantiomer of compound (I) with the S enantiomer of compound (II). Alternatively, the (S,S)-diastereomer of compound (III) is prepared by reacting the S enantiomer of compound (I) with the S enantiomer of compound (II). Alternatively, the (S,R)-diastereomer of compound (III) is prepared by reacting the S enantiomer of compound (I) with the R enantiomer of compound (II).

In an embodiment, $R_1$ is straight chain or branched alkyl, for example, $C_1$-$C_{10}$ alkyl, such as methyl, ethyl, n-propyl, isopropyl, n-butyl, isobutyl, sec-butyl, tert-butyl, straight- or branched-pentyl, straight- or branched-hexyl, straight- or branched-heptyl, straight- or branched-nonyl or straight- or branched-decyl. Suitably, alkyl is $C_1$-$C_4$ alkyl.

In an embodiment, $R_1$ is $C_6$-$C_{14}$ aryl, preferably $C_6$-$C_{10}$ aryl. The aryl group may be substituted by at least one group selected from mercapto, dialkylamino, nitro, alkoxy, halogen, keto, cyano or a combination. Preferably aryl is benzyl.

The term "alkoxy" means "alkyloxy", wherein "alkyl" has the same meanings as given above. In an embodiment, $R_1$ is straight chain or branched alkoxy, for example $C_1$-$C_{10}$ alkoxy, such as methoxy, ethoxy, n-propoxy, isopropoxy, n-butoxy, isobutoxy, sec-butoxy, tert-butoxy or straight- or branched-pentoxy, -hexyloxy, -heptyloxy, -octyloxy, -nonyloxy or -decyloxy. Suitably, R1 is $C_1$-$C_4$ alkoxy.

In an embodiment, $R_1$ is $C_3$-$C_{10}$ cycloalkyl having 3- to 8-ring carbon atoms, for example cyclopropyl, cyclobutyl, cyclopentyl, cyclohexyl, cycloheptyl or cycloheptyl, any of which may be substituted by one, two or more substituents such as $C_1$-$C_4$ alkyl groups, particularly methyl groups. Suitably, $R_1$ is $C_3$-$C_6$ cycloalkyl.

In an embodiment, $R_1$ is a monovalent heterocyclic group having up to 20 carbon atoms and one, two, three or four heteroatoms selected from nitrogen, oxygen and sulfur, the group optionally having an alkyl, alkylcarbonyl, hydroxyalkyl, alkoxyalkyl or aralkyl group attached to a ring carbon or nitrogen atom and being linked to the remainder of the molecule through a ring carbon atom, for example a group, preferably a monocyclic group, with one nitrogen, oxygen or sulfur atom, such as pyrryl, pyridyl, piperidyl, furyl, tetrahydrofuryl or thienyl, or a group, preferably a monocyclic group, with two hetero atoms selected from nitrogen, oxygen and sulfur, such as imidazolyl, pyrimidinyl, piperazinyl, oxazolyl, isoxazolyl, thiazolyl, morpholinyl or thiomorpholinyl. Suitably, heterocyclic is a monocyclic group having 5- or 6-ring atoms and one or two nitrogen atoms, or one nitrogen atom and one oxygen atom, in the ring and optionally substituted on a ring nitrogen atom by $C_1$-$C_4$ alkyl, hydroxy $C_1$-$C_4$ alkyl, $C_1$-$C_4$ alkylcarbonyl or phenyl $C_1$-$C_4$ alkyl.

In an embodiment, $R_1$ is straight chain or branched-alkenyl, for example $C_2$-$C_{10}$ alkenyl, for example vinyl, 1-propenyl, 2-propenyl, 1-butenyl, isobutenyl, or straight- or branched-pentenyl, -hexenyl, -heptenyl, -octenyl, -nonenyl or -decenyl. Suitably, $R_1$ is $C_2$-$C_4$ alkenyl.

In an embodiment, $R_1$ is benzocycloalkyl wherein cycloalkyl is as defined above, attached at two adjacent carbon atoms to a benzene ring. Suitably, $R_1$ is benzo-$C_5$-$C_6$-cycloalkyl, or benzocyclohexyl (tetrahydronaphthyl).

In an embodiment, $R_1$ is aralkyl meaning arylalkyl, wherein aryl and alkyl have the same meanings as given above, such as straight- or branched-chain $C_6$-$C_{10}$ aryl-$C_1$-$C_{10}$ alkyl, for example one of the $C_1$-$C_{10}$ alkyl groups mentioned above, particularly one of the $C_1$-$C_4$ alkyl groups, substituted by phenyl, tolyl, xylyl or naphthyl. Suitably, aralkyl is phenyl-$C_1$-$C_4$ alkyl, particularly benzyl or 2-phenylethyl.

In an embodiment, $R_1$ is haloalkyl wherein alkyl is as defined above substituted by one or more, for example one, two or three, halogen atoms, preferably fluorine or chlorine atoms. Suitably, $R_1$ is $C_1$-$C_4$ alkyl substituted by one, two or three fluorine or chlorine atoms.

In an embodiment, $R_1$ is haloarylalkyl wherein aralkyl is as defined above, substituted by one or more heterocyclic groups as defined above.

In an embodiment, $R_1$ is heteroaralkyl wherein aralkyl is as defined above wherein one, two, three or four carbon atoms are replaced with heteroatoms selected from nitrogen, oxygen and sulfur.

In an embodiment, $R_1$ is alkoxyaralkyl wherein alkoxy and aralkyl have the same definitions as given above.

In an embodiment, $R_1$ is substituted silyl group wherein the silyl group is substituted with at least one alkyl group as defined above.

In an embodiment, the salt of compound (II) is the hydrochloride salt.

In an embodiment, $R_2$ is optionally substituted silyl, $R_2'$ is optionally substituted silyl and $R_3$ is hydrogen. In an embodiment, $R_2$ and $R_2'$ are silyl. Suitably, $R_2$ and $R_2'$ are trialkylsilyl, wherein alkyl has the same meanings as given above and each alkyl may be the same or different. Suitably, the silyl group is selected from the group consisting of trimethylsilyl, triethylsilyl and t-butyldimethylsilyl. Alternatively, $R_2$ may be diarylalkylsilyl, wherein aryl and alkyl have the same meanings as given above and each aryl may be the same or different. Suitably, the diarylalkylsilyl is t-butyldiphenylsilyl.

In an alternative embodiment, $R_2$ is optionally substituted silyl, $R_2'$ is hydrogen and $R_3$ is optionally substituted silyl. In an embodiment, $R_2$ and $R_3$ are silyl. Suitably, $R_2$ and $R_3$ are trialkylsilyl, wherein alkyl has the same meanings as given above and each alkyl may be the same or different. Suitably, the silyl group is selected from the group consisting of trimethylsilyl, triethylsilyl and t-butyldimethylsilyl. Alternatively, $R_3$ may be diarylalkylsilyl, wherein aryl and alkyl have the same meanings as given above and each aryl may be the same or different. Suitably, the diarylalkylsilyl is t-butyldiphenylsilyl.

In a further embodiment, $R_2$, $R_2'$ and $R_3$ are all optionally substituted silyl, preferably silyl. Suitably, the silyl is trialkylsilyl, wherein alkyl has the same meanings as given above and each alkyl may be the same or different. Suitably, the silyl group is selected from the group consisting of trimethylsilyl, triethylsilyl and t-butyldimethylsilyl. Alternatively, the silyl may be diarylalkylsilyl, wherein aryl and alkyl have the same meanings as given above and each aryl may be the same or different. Suitably, the diarylalkylsilyl is t-butyldiphenylsilyl.

In an alternative embodiment, $R_2$ is benzyl, $R_2'$ is hydrogen and $R_3$ is benzyl.

In another embodiment, $R_2$ is hydrogen, $R_2'$ is hydrogen and $R_3$ is hydrogen.

In an embodiment, compounds (I) and (II) are optically pure. Throughout this specification "optically pure" is to mean having an enantiomeric excess greater than 97%. Preferably greater than 98%, most preferably greater than 99%.

In an embodiment, the condensation is carried out in the presence of a solvent. The solvent may be an organic solvent, for example the organic solvent may be selected from the group consisting of methanol, ethanol, isopropyl alcohol (IPA), t-butanol, methyl isobutylketone, toluene, t-amylalcohol, acetonitrile, diglyme, dimethylsulphoxide (DMSO) xylene and hexamethylphosphoramide (HMPA). Alternatively, the condensation may be carried out in the absence of solvent. In this embodiment, the condensation is suitably carried out at a temperature ranging from about 100 to about 140° C.

In an embodiment, the condensation step is carried out below 140° C., suitably below 120° C.

In another embodiment, the condensation step is carried out in the presence of a base. The base may be an organic base or an inorganic base. The base may be selected from triethylamine, potassium carbonate, sodium carbonate and diisopropylethylamine.

In an embodiment, $R_2$ is silyl and the compound of formula (II) is designated (IIa). It has surprisingly been found that the use of the silylated compound of formula (IIa) minimizes the formation of the dimeric impurity and regioisomer.

The compound of formula (IIa) may be obtained by reacting the compound of formula (II) wherein $R_2$ is hydrogen (designated compound (IIc)) with a suitable silylating agent. The silylating agent comprises a silyl group and may comprise a trialkylsilyl group, wherein the term "trialkylsilyl" has the same meaning as given above. Alternatively, the silylating agent may comprise a diarylalkylsilyl group, wherein the term "diarylalkylsilyl" has the same meaning as given above. In an embodiment, the silyl group is selected from the group consisting of trimethylsilyl, triethylsilyl, t-butyldiphenylsilyl and t-butyldimethylsilyl.

The compound of formula (IIc) can be made by any process known in the art, for example as described in U.S. Pat. No. 4,579,854.

In an embodiment, the compound of formula (IIa) is condensed with the compound of formula (I) wherein $R_1$ is benzyl, optionally at about 110° C., to give the corresponding compound of formula (III).

In another embodiment, $R_2$ is substituted benzyl and the compound of formula (II) is designated (IIb). It has surprisingly been found that the use of the benzylated compound of formula (IIb) minimizes the formation of the dimeric impurity and regioisomer. The substituent(s) may be selected from the group consisting of: halo, such as fluoro, chloro, bromo, or iodo; alkoxy such as methoxy; and nitro. In an embodiment, $R_2$ is pentafluorobenzyl (i.e. five fluoro substituents). Suitably, there is one halo, alkoxy or nitro group situated at the 4-position (i.e. the para position).

In another embodiment, the condensation step is carried out in a solvent, preferably HMPA, which minimizes the formation of the dimeric impurity and regioisomer.

Further, in yet another embodiment, when $R_1$ is not silyl, the reaction is carried out using HMPA solvent preferably at a temperature below 100° C. It has surprisingly been found that these reaction conditions minimize the formation of the dimeric impurity and regioisomer.

The compound of formula (IIb) may be synthesized by using methods known in the prior art.

In an embodiment, compound (I) is prepared by converting a compound of formula (Ig) to the compound (I). The conversion may be according to any process described in this specification.

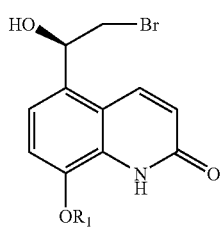

(Ig)

In an embodiment, compound (Ig) is prepared by converting a compound of formula (If) to the compound (Ig). The conversion may be according to any process described in this specification.

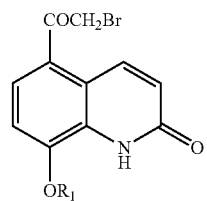

(If)

In an embodiment, compound (If) is prepared by converting a compound of formula (Ie) to the compound (If). The conversion may be according to any process described in this specification.

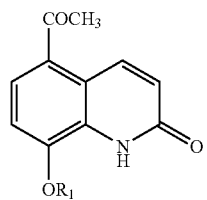

(Ie)

In an embodiment, compound (Ie) is prepared by converting a compound of formula (Id) to the compound (Ie). The conversion may be according to any process described in this specification.

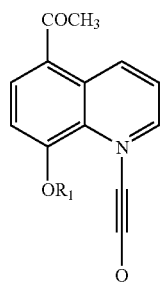

(Id)

In an embodiment, compound (Id) is prepared by converting a compound of formula (Ic) to the compound (Id). The conversion may be according to any process described in this specification.

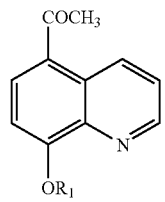

(Ic)

In an embodiment, compound (Ic) is prepared by converting a compound of formula (Ib) to the compound (Ic). The conversion may be according to any process described in this specification.

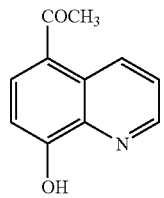

(Ib)

In an embodiment, compound (Ib) is prepared by converting a compound of formula (Ia) to the compound (Ib). The conversion may be according to any process described in this specification.

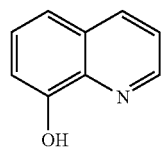

(Ia)

The process of the present invention may further comprise converting the (R,R)—, (S,S)—, (R,S)— or (S,R)-diastereomer of compound of formula (III) to the corresponding (R,R)—, (S,S)—, (R,S)— or (S,R)-diastereomer of carmoterol.

In an embodiment, the (R,R)—, (S,S)—, (R,S)— or (S,R)-diastereomer of the compound of formula (III) is hydrolyzed in the presence of an acid to obtain the corresponding (R,R)—, (S,S)—, (R,S)— or (S,R)-diastereomer of a compound of formula (IV)

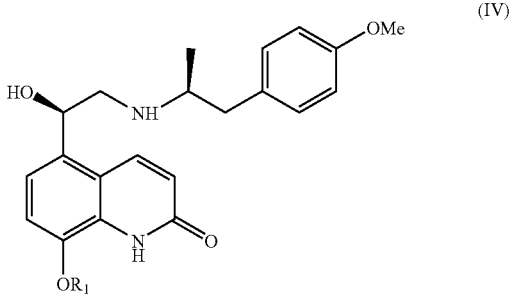

(IV)

The acid may be a carboxylic acid, such as benzoic acid, oxalic acid, maleic acid, succinic acid, fumaric acid or tartaric acid; or a mineral acid, such as hydrochloric acid. Other acids include salicylic acid, di-p-toluoyl-D-tartaric acid, di-benzoyl-D-tartaric acid, di-pivaloyl-D-tartaric acid, glutamic acid, ethylenediaminetetraacetic acid, mandelic acid, malonic acid, acetic acid, anthranilic acid, nicotinic acid and furoic acid.

The condensation and hydrolyzation steps may be carried out without isolation of the compound (III).

The compound (IV) may be isolated in the form of its acid addition salt as a compound of formula (V)

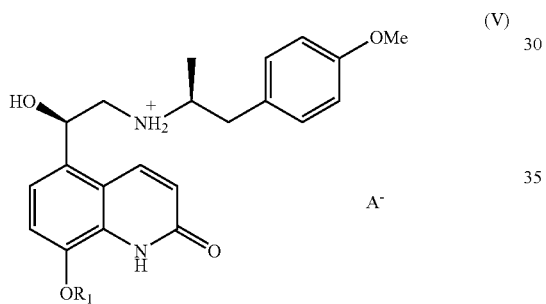

(V)

wherein $R_1$ is as defined above and $A^-$ is an anion. The anion corresponds to the acid used in the hydrolysation step. Thus, the anion may be selected from oxalate, fumarate, tartrate, benzoate, salicylate, di-p-toluoyl D-tartrate, di-benzoyl D-tartrate, di-pivaloyl D-tartrate, succinate, glutamate, ethylenediaminetetraacetate, maleate, mandelate, malonate, acetate, anthranilate, nicotinate and furoate.

In an embodiment, the compound of formula (IV) or (V) is isolated by crystallization. Suitably, the crystallisation of (V) involves converting the acid addition salt to a different salt, such as the hydrochloride salt. The conversion of the acid addition salt may either involve isolation of the free base or no isolation of the free base.

In a further embodiment, the (R,R)—, (S,S)—, (R,S)— or (S,R)-diastereomer of the compound of formula (IV) or (V) is converted to the corresponding (R,R)—, (S,S)—, (R,S)— or (S,R)-diastereomer of carmoterol. Suitably, the conversion comprises deprotection of the $OR_1$ group using a suitable deprotecting reagent. As is well known to the skilled person, the deprotection reagent depends on the nature of the protecting group.

The hydrolyzation and deprotection steps may be carried out without isolation of the compound (IV) or (V).

The condensation, hydrolyzation and deprotection steps may be carried out without isolation of the compounds (III) and (IV) or (V).

When $R_1$ is a benzylic group, the deprotection may comprise hydrogenolysis of the compound of formula (IV) or (V) in the presence of a noble metal catalyst and hydrogen gas.

Alternatively, other deprotecting reagents may be used, such as mineral acids, strong acids, Lewis acids or aqueous mineral bases in a suitable solvent.

When $R_1$ is substituted silyl, the deprotection may comprise treating the compound of formula (IV) or (V) with t-butylammonium fluoride or potassium fluoride.

When $R_1$ is arylalkyl or substituted arylalkyl, the deprotection may comprise catalytic reduction using palladium-based or platinum-based catalysts such as palladium, palladium hydroxide, palladium on activated carbon, palladium on alumina, platinum, platinum on activated carbon and Raney nickel.

In an embodiment, the deprotection of compound (IV) or (V) is carried out in the presence of a solvent. The solvent may be selected from an organic solvent such as an alkyl acetate, lower alkylamines for example $C_1$ to $C_6$ alkylamines, alcohols, aliphatic hydrocarbons, aromatic hydrocarbons, heterocycles or dialkylethers, an acid, a mixture of water and a water miscible solvent, ionic liquids, halogenated solvents and mixtures thereof.

In a further embodiment, the R,R-carmoterol base is converted to a pharmaceutically acceptable salt thereof.

According to another aspect of the present invention, there is provided a process for preparing the (R,R)—, (S,S)—, (R,S)— or (S,R)-diastereomer of carmoterol comprising converting the corresponding (R,R)—, (S,S)—, (R,S)— or (S,R)-diastereomer of a compound of formula (III) to the compound of formula (V) in the presence of an acid having the formula HA,

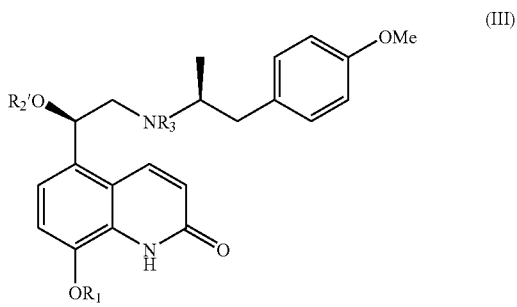

(III)

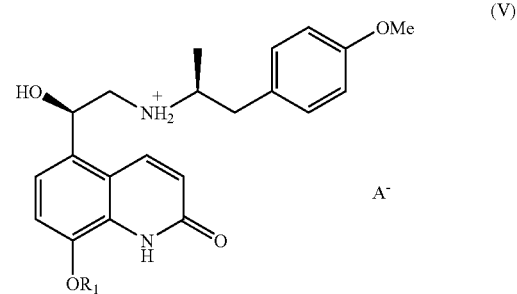

(V)

wherein $R_1$, $R_2$, $R_2'$, $R_3$ and $A^-$ have the same meanings as given above. The acid may be a carboxylic acid, such as benzoic acid, oxalic acid, maleic acid, succinic acid, fumaric acid or tartaric acid; or a mineral acid, such as hydrochloric acid. Other acids include salicylic acid, di-p-toluoyl-D-tartaric acid, di-benzoyl-D-tartaric acid, di-pivaloyl-D-tartaric acid, glutamic acid, ethylenediaminetetraacetic acid, mandelic acid, malonic acid, acetic acid, anthranilic acid, nicotinic acid and furoic acid.

In an embodiment, the (R,R)-diastereomer of the compound of formula (III) is converted to (R,R)-carmoterol.

According to another aspect of the present invention, there is provided the R or S enantiomer of a compound of formula (II)

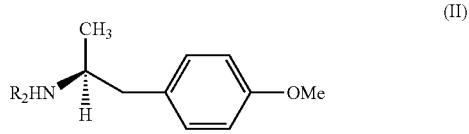

wherein $R_2$ is optionally substituted silyl.

In an embodiment, compound of formula (II) is in the form of the R enantiomer.

In an embodiment, $R_2$ is silyl. In an embodiment, $R_2$ is a trialkylsilyl group, wherein the term "alkyl" has the same meaning as given above and each alkyl may be the same or different. In an embodiment, the trialkylsilyl group is selected from the group consisting of trimethylsilyl, triethylsilyl and t-butyldimethylsilyl. Alternatively, $R_2$ may be diarylalkylsilyl, wherein aryl and alkyl have the same meanings as given above and each aryl may be the same or different. Suitably, the diarylalkylsilyl is t-butyldiphenylsilyl.

According to another aspect of the present invention, there is provided a process for preparing the R or S enantiomer of a compound of formula (II)

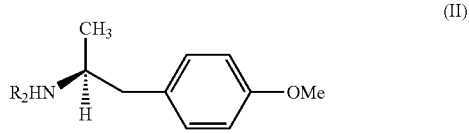

wherein $R_2$ is optionally substituted silyl, comprising converting (R)—N-(2-(p-methoxyphenyl)-1-methylethyl)amine to the compound of formula (II).

In an embodiment, compound of formula (II) is in the form of the R enantiomer.

In an embodiment, $R_2$ is silyl and the conversion comprises reacting (R)—N-(2-(p-methoxyphenyl)-1-methylethyl)amine with a suitable silylating agent. The silylating agent comprises a silyl group and may comprise a trialkylsilyl group or a diarylalkylsilyl group, wherein the terms "trialkylsilyl" and "diarylalkyl silyl" have the same meanings as given above. In an embodiment, the silyl group is selected from the group consisting of trimethylsilyl, triethylsilyl, t-butyldiphenylsilyl and t-butyldimethylsilyl. The silylating agent may be hexamethyldisilazane (to form compound (II) wherein $R_2$ is trimethylsilyl) or hexaethyldisilazane (to form compound (II) wherein $R_2$ is triethylsilyl).

The (R)—N-(2-(p-methoxyphenyl)-1-methylethyl)amine may be made by any process known in the art, for example as described in U.S. Pat. No. 4,579,854.

Alternatively, the (R)—N-(2-(p-methoxyphenyl)-1-methylethyl)amine may be prepared by resolving 4-methoxyphenylacetone using R-(+)-phenyl ethyl amine in the presence of a first reducing agent to produce (R)-(+)-N-(1-phenylethyl)-N-[1-(p-methoxyphenyl)-2-propyl)]amine, optionally converting the (R) — (+)—N-(1-phenylethyl)-N-[1-(p-methoxyphenyl)-2-propyl)]amine hydrochloride to a salt such as the hydrochloride salt, followed by converting the (R)-(+)-N-(1-phenylethyl)-N-[1-(p-methoxyphenyl)-2-propyl)]amine or salt thereof to the (R)—N-(2-(p-methoxyphenyl)-1-methylethyl)amine in the presence of a second reducing agent.

In an embodiment, the first reducing agent is Raney Nickel and methanol.

In an embodiment, the second reducing agent is 10% palladium on carbon and methanol.

According to another aspect of the present invention, there is provided a process for preparing the R or S enantiomer of a compound of formula (I) comprising subjecting a compound of formula (If) to chiral reduction to form the R or S enantiomer of a compound of formula (Ig) followed by cyclisation to the R or S enantiomer of the compound of formula (I)

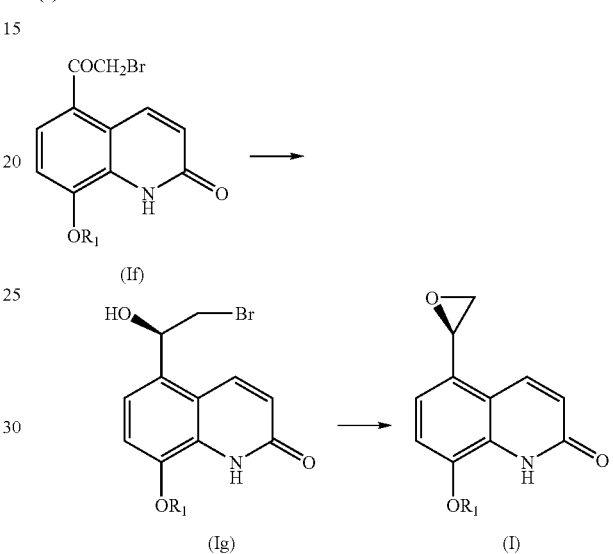

wherein $R_1$ has the same meanings as given above.

In an embodiment, the R enantiomer of the compound of formula (I) is prepared by subjecting the compound of formula (If) to chiral reduction to form the R enantiomer of the compound of formula (Ig) followed by cyclisation to the R enantiomer of the compound of formula (I).

In an embodiment, the S enantiomer of the compound of formula (I) is prepared by subjecting the compound of formula (If) to chiral reduction to form the S enantiomer of the compound of formula (Ig) followed by cyclisation to the S enantiomer of the compound of formula (I).

In an embodiment, the bromoacetyl compound (If) is subjected to chiral reduction using a chiral reducing agent selected from the group consisting of (−)-DIP-chloride, β-isopinocamphinyl-9BBN (R-Alpine-Borane), a chiral β-oxoaldiminatocobalt (II) complex and a borane reducing agent, and optionally in the presence of a catalytic amount of a single enantiomer of an oxazaborolidine derived from a chiral oxazaborolidine catalyst.

Suitably, the chiral reducing agent is a chiral β-oxoaldiminatocobalt (II) complex, and the complex is present in an amount of about 1 mol %.

Suitably, the chiral reducing agent is a borane reducing agent, and the borane reducing agent is present in about one equivalent.

In an embodiment, the borane reducing agent is $BH_3 \cdot THF$ (THF=tetrahydrofuran) or borane-methyl sulfide.

In an embodiment, the chiral oxazaborolidine catalyst is selected from the group consisting of cis-(1R,2S)-aminoindanol, R-diphenyl prolinol, R-methyl oxazaborolidene (derived from R-diphenyl prolinol, trimethylboroxine and methyl boronic acid) and non-α-substituted (R)-indoline-2-carboxylic acid. The oxazaborolidine catalyst may be generated in situ from R-diphenyl prolinol and diborane.

The reduction is highly enantioselective (a single isomer is typically formed with an enantiomeric excess greater than 98% ee even when using a low mol % of the catalyst per mole of ketone (If). In an embodiment, the oxazaborolidine catalyst is present in an amount ranging from about 5 to about 10 mol % per mole of ketone (If).

In an embodiment, compound of formula (Ig) is treated with at least one equivalent of a base to produce the compound of formula (I). The base may be an organic base or inorganic bases. Suitably, the base may be aqueous NaOH or $K_2CO_3$. Optionally, the aqueous NaOH or $K_2CO_3$ is present in an alcohol solvent or solvent mixture such as MeOH/TH, acetone/THF. Alternatively, the base is piperidine, pyridine or pyrrolidine, preferably piperidine.

In an embodiment, the compound of formula (I) is obtained without isolation of the compound of formula (Ig).

The compound of formula (I) may be purified by recrystallisation from an inert organic solvent.

In an embodiment, the compound of formula (I) used to prepare the compound of formula (III) as described above is prepared according to the process as described above.

In an embodiment, the compound of formula (If) is prepared by brominating a compound of formula (Ie) in the presence of a brominating agent

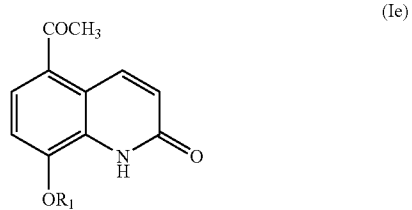

(Ie)

wherein $R_1$ has the same meanings as given above.

In an embodiment, the brominating agent is N-bromosuccinimide or bromine. The brominating agent may be present in a solvent selected from the group consisting of tetrahydrofuran, methylene chloride, chloroform, methanol, carbon tetrachloride, or a mixture thereof; preferably dichloromethane.

According to another aspect of the present invention, there is provided a process for preparing a compound of formula (Ie) comprising heating a compound of formula (Id) in the presence of a reagent

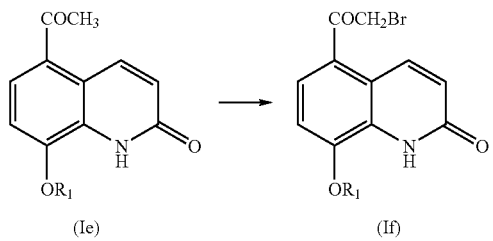

(Ie)     (If)

wherein $R_1$ has the same meanings as given above and the reagent is present in a volume ranging from about 1.5 volumes to about 5 volumes.

A "volume" refers to the volume of the solvent (in ml) used per gram of the compound being dissolved.

In U.S. Pat. No. 4,579,854 (column 21, preparation 1), 5 grams of 5-acetyl-8-benzyloxyquinoline is used to produce 5 acetyl-8-benzyloxyquinoline-N-oxide. Theoretically, 5 grams of 5-acetyl-8-benzyloxyquinoline (compound (Ic) wherein $R_1$ is benzyl) will yield 5.27 grams of 5 acetyl-8-benzyloxyquinoline-N-oxide (compound (Id) wherein $R_1$ is benzyl). The 5 acetyl-8-benzyloxyquinoline-N-oxide is stirred in 60 ml acetic anhydride. This corresponds to 11.3 volumes of acetic anhydride. It has surprisingly been found that a smaller number of volumes of reagent can be used in the process of the present invention. For example, 10 grams of 5-Acetyl-8-benzyloxycarbostyril are dissolved in 20 ml of acetic anhydride, i.e. 2 volumes of acetic anhydride. This avoids the handling of a large quantity of solvent. The work up procedure required is simplified to give the product in high purity and it also minimizes the formation of impurities which are formed when the work up procedure given in the prior art is employed.

In an embodiment, the reagent is present in a volume ranging from about 1.5 volumes to about 3 volumes, preferably 2 volumes.

In an embodiment, the reagent is an anhydride, suitably acetic anhydride or trifluoroacetic anhydride, preferably acetic anhydride. Most preferably, the reagent is acetic anhydride present in about 2 volumes.

In an embodiment, the compound of formula (Ie) used to prepare the compound of formula (If) as described above is prepared according to the process described above.

According to another aspect of the present invention, there is a provided a process for preparing a compound of formula (Id) comprising oxidising a compound of formula (Ic) in the presence of an oxidizing agent and a solvent selected from dichloromethane, ethyl acetate or a mixture thereof

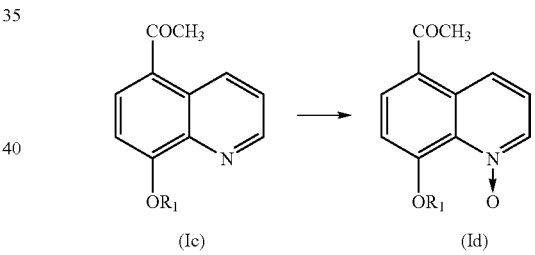

(Ic)     (Id)

wherein $R_1$ has the same meanings as given above.

In an embodiment, the oxidizing agent is selected from the group consisting of: peracids such as peroxybenzoic acid, m-chloroperbenzoic acid, peracetic acid, peroxytrifluoroacetic acid, peroxysulfuric acid, perboric acid, performic acid, peroxymaleic acid and peroxydichloromaleic acid (for example, prepared from hydrogen peroxide and dichloromaleic anhydride); tert-butyl hydroperoxide in the presence of a vanadium catalyst; dimethyl dioxirane; selenium dioxide; m-phenanthroline di-N-oxide (for example prepared from $H_2O_2$ and m-phenanthroline); nitric acid and hydrogen peroxide. Preferably, the oxidizing agent is m-chloroperoxybenzoic acid.

In U.S. Pat. No. 4,579,854, chloroform is used as solvent and the reaction time is 95.5 hours. It has surprisingly been found that the use of dichloromethane, ethyl acetate or a mixture thereof as solvent drastically reduces the reaction time, for example to around 5 hours.

In an embodiment, the process for preparing compound (Id) is carried out for a period of time less than 10 hours, preferably less than 8 hours, more preferably less than 6 hours.

In an embodiment, the compound of formula (Id) used to prepare the compound of formula (Ie) as described above is prepared according to the process described above.

According to another aspect of the present invention, there is a provided a process for preparing a compound of formula (Ic) comprising reacting a compound of formula (Ib) with a protecting group in the presence of a low boiling point solvent

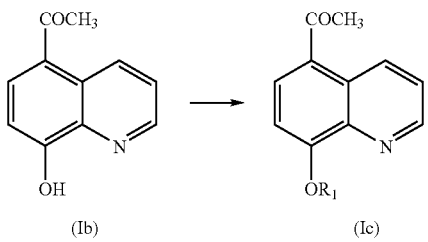

wherein $R_1$ has the same meanings as given above.

The low boiling solvent may have a boiling point below 70° C., preferably below 60° C. In an embodiment, the solvent is acetone.

Suitable protecting groups for hydroxy groups are well known to those skilled in the art and include a compound comprising a group selected from lower alkanoyl for example a $C_1$ to $C_6$ alkanoyl, substituted or unsubstituted benzyl and substituted or unsubstituted phenyl. Preferably, the protecting agent is benzyl bromide and this results in the work up procedure being simplified by distillation, avoiding any extraction procedure.

In U.S. Pat. No. 4,579,854, benzyl chloride is used as the protecting reagent, and this necessitates that the reaction mass be extracted in ethyl acetate (see U.S. Pat. No. 4,579,854, column 20, preparation 1). Furthermore, the prior art reaction is carried out using a high boiling solvent such as DMF. The process of the present invention uses a low boiling solvent, such as acetone. This also results in the work up procedure being simplified by distillation, avoiding any extraction procedure.

In an embodiment, the compound of formula (Ic) used to prepare the compound of formula (Id) as described above is prepared according to the process described above.

According to another aspect of the present invention, there is a provided a process for preparing a compound of formula (Ib) comprising acylating a compound of formula (Ia) with an acylating agent and an acid catalyst in the presence of a low boiling point solvent

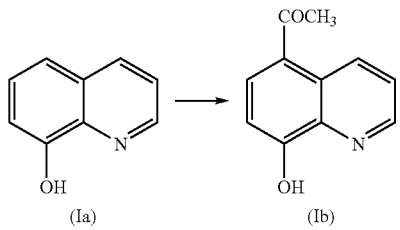

The low boiling solvent may have a boiling point below 90° C., preferably below 80° C. The solvent used is preferably selected from a halogenated solvent, carbon disulfide and mixtures thereof, preferably dichloroethane. The solvent used for the above process of invention is advantageous over solvents used in the prior art (for example, Journal of American Chemical Society 1930, Vol 52, pp 4433-4436, which uses nitrobenzene) in that the latter are high-boiling point, hazardous solvents that require steam distillation to be removed, in order to isolate the product. The product of the process of the present invention is easily isolated, for example by quenching the reaction mass in water and optionally converting the product to base.

In an embodiment, the acylating agent is a haloacetyl compound, wherein halo is chloro, bromo, iodo or fluoro, preferably chloro.

In an embodiment, the acid catalyst is a Lewis acid catalyst, for example boron trichloride, aluminum chloride, titanium tetrachloride, boron trifluoride, tin tetrachloride or zinc chloride.

In an embodiment, the compound of formula (Ib) used to prepare the compound of formula (Ic) as described above is prepared according to the process described above.

According to another aspect of the present invention, there is provided (R,R)-carmoterol prepared according to the process described above. The intermediates (Ib) to (Ig), (I), (II), (IV) and (V) prepared according to the processes described above also form further aspects of the present invention.

According to another aspect of the present invention, there is provided a pharmaceutical composition comprising (R,R)-carmoterol as described above together with one or more pharmaceutically acceptable excipients.

According to yet another aspect of the present invention, there is provided the use of (R,R)-carmoterol as described above in medicine.

According to a still further aspect of the present invention, there is provided the use of (R,R)-carmoterol as described above in the treatment of asthma or chronic obstructive pulmonary disease (COPD). A study, conducted over an 8-day treatment period, has shown that carmoterol provides significant improvements in lung function.

According to a still further aspect of the present invention, there is provided the use of (R,R)-carmoterol as described above in the manufacture of a medicament for the treatment of asthma or chronic obstructive pulmonary disease (COPD).

According to another aspect of the present invention, there is provided a method of treating asthma and chronic obstructive pulmonary disease (COPD) comprising administering to a patient in need thereof (R,R)-carmoterol as described above.

DETAILED DESCRIPTION

The present invention provides an improved process for the synthesis of optically pure carmoterol, more particularly (R,R) and (S,S)-carmoterol.

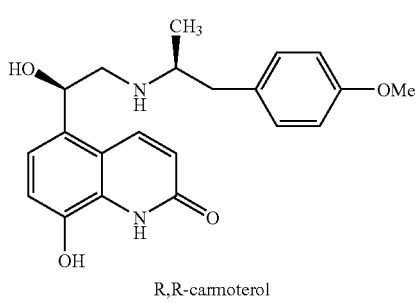

R,R-carmoterol

-continued

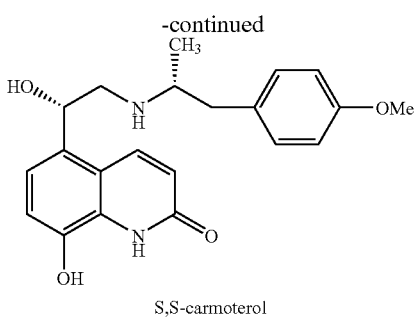

S,S-carmoterol

In its broadest aspect, the invention relates to a process for preparing compound (III) (a precursor to carmoterol) or a salt thereof, which comprises the steps of:
(i) condensing an optically pure oxiranyl compound of formula (I)

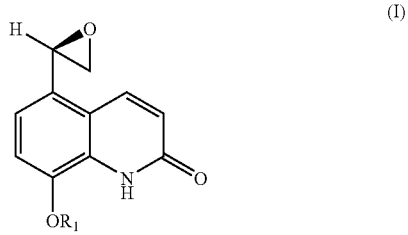

(I)

wherein R₁=alkyl, aryl, allyl, alkoxy, cycloalkyl, heterocyclic, alkenyl, benzocycloalkyl, aralkyl, haloaryalkyl, heteroaralkyl, haloalkyl, aralkyl, alkoxyaralkyl, substituted benzyl, substituted silyl group;
with an optically pure amine of formula (II)

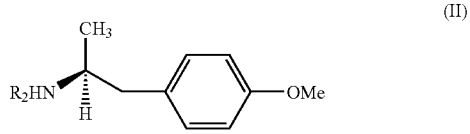

(II)

wherein a —R₂=optionally substituted silyl group or
b–R₂=optionally substituted benzyl group or
c–R₂=hydrogen;
to obtain a compound of formula (III) which can be optionally isolated.

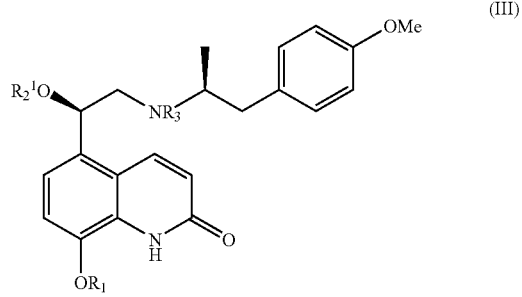

(III)

When R₂ is optionally substituted silyl, either R₂' and R₃ are the same as R₂; R₂' is the same as R₂ and R₃ is hydrogen; or R₂' is hydrogen and R₃ is the same as R₂; when R₂ is optionally substituted benzyl, R₂' is hydrogen and R₃ is the same as R₂; and when R₂ is hydrogen, R₂' is hydrogen and R₃ is hydrogen.

Typically, the compound of formula (I) is condensed with the compound of formula (II) in a solvent such as methanol, ethanol, isopropyl alcohol (IPA), t-butanol, methyl isobutylketone, toluene, t-amylalcohol, acetonitrile, diglyme, dimethylsulphoxide (DMSO) xylene or HMPA below 140° C. This reaction can be optionally carried out in the absence of solvent at a temperature ranging from about 100 to about 140° C., to give an optically pure compound (III). Further, this reaction can also be carried out optionally in the presence of, either organic or inorganic base, such as triethylamine, potassium carbonate, sodium carbonate, diisopropylethylamine to accelerate the reaction.

More particularly, the compound of formula (IIa) wherein R₂ is silyl, may be condensed with the compound of formula (I) wherein R₁ is benzyl at about 110° C., to give the corresponding compound of formula (III) in a substantially pure form. Use of the silylated compound of formula (IIa) minimizes the formation of the dimeric impurity and regio isomer, this forms another aspect of the present invention. The compound of formula (IIa) can be obtained by reacting the compound of formula (IIc) with a suitable silylating agent. The suitable silylating agent used to protect the amine functionality may comprise a group selected from trimethylsilyl, triethylsilyl, t-butyldiphenylsilyl, t-butyldimethylsilyl, etc. The compound of formula (IIc) can be made by any process known in the art.

The process of the present invention may further comprise (ii) hydrolyzing the compound of formula (III) with an acid to obtain a compound of formula (IV)

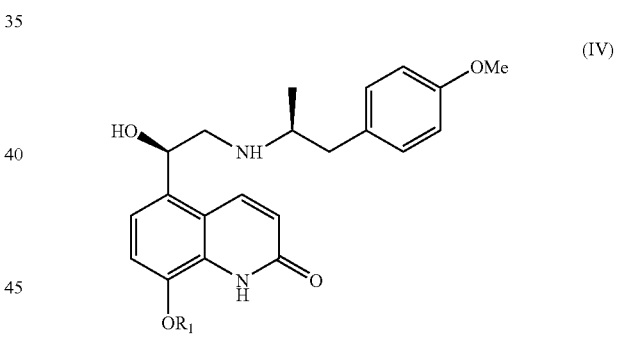

(IV)

Steps (i) and (ii) may be carried out without isolation of the compound (III).

The compound (IV) may be isolated in the form of its acid addition salt of compound of formula (V).

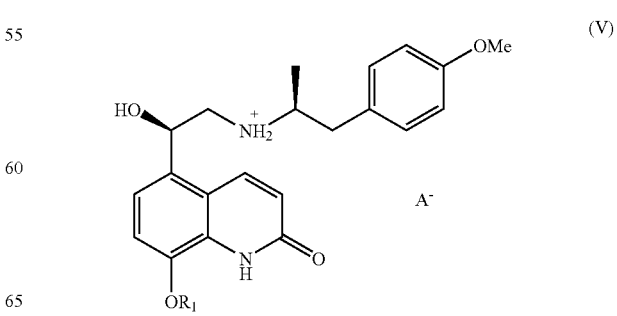

(V)

wherein $R_1$ is as defined above and $A^-$ is an anion. The anion corresponds to the acid. The acid optionally used in step (ii) is preferably a carboxylic acid, such as benzoic acid, oxalic acid, maleic acid, succinic acid, fumaric acid or tartaric acid; or a mineral acid, such as hydrochloric acid.

The compound of formula (IV) or (V) may be isolated by crystallization. Crystallization helps in eliminating the impurities associated with the reaction, as it reduces the amount of regioisomer formed during the condensation step. The acid addition salt may be converted to a different salt, such as the hydrochloride salt. The conversion of the acid addition salt may either involve isolation of the free base or no isolation of the free base. This conversion further reduces dimeric and regio isomeric impurities below the detection limit.

The process of the present invention may further comprise (iii) deprotection of the $OR_1$ group under suitable deprotecting conditions. As is well known to the skilled person, the deprotection conditions depend on the nature of the protecting group. For example, the deprotection may involve hydrogenolysis of the compound of formula (V) in the presence of a noble metal catalyst and hydrogen gas or using a phase transfer hydrogenation, to obtain optically pure R,R-carmoterol base. Alternatively other deprotecting reagents may be used, such as mineral acids, strong acids, Lewis acids or aqueous mineral bases in a suitable solvent.

When $R_1$ is substituted silyl, a preferred method for deprotection is by treating the compound of formula (V) with t-butylammonium fluoride or potassium fluoride.

When $R_1$ is arylalkyl or substituted arylalkyl, a preferred method for deprotection is catalytic reduction using catalysts such as palladium, palladium hydroxide, palladium on activated carbon, palladium on alumina, platinum, platinum on activated carbon and Raney nickel.

The solvent used in step (iii) is preferably selected from an alkyl acetate, lower alkylamines, alcohols, aliphatic hydrocarbons, aromatic hydrocarbons, heterocycles, dialkylethers, an acid, mixture of water and water miscible solvents, ionic liquids, halogenated solvents and mixtures thereof.

The process of the present invention may further comprise: (iv) converting R,R-carmoterol base to a pharmaceutically acceptable salt thereof.

Alternatively, (R,R)-carmoterol may be synthesized by reacting a compound of formula (IIb), wherein $R_2$ is substituted benzyl, with a compound of formula (I), followed by debenzylation.

The compound of formula (IIb) may be synthesized by using methods known in the prior art.

The compound of formula (I) may be prepared from a bromoacetyl compound of formula (If) as shown in Scheme 2.

Scheme 2

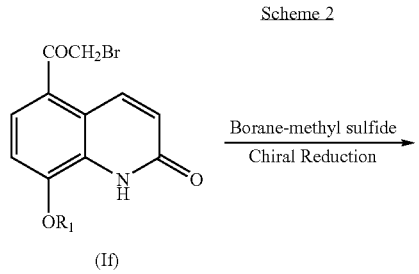

(If)

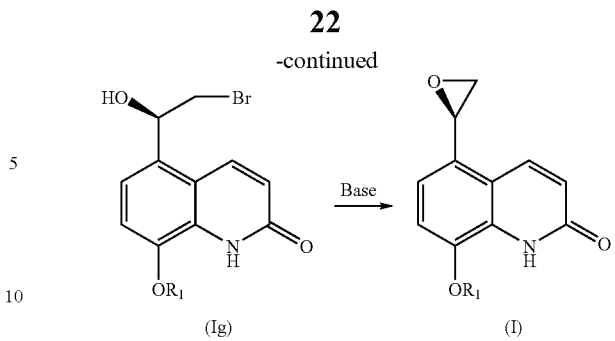

wherein the bromoacetyl compound is subjected to chiral reduction using chiral reducing agents such as (−)-DIP-chloride, β-isopinocamphinyl-9BBN (R-Alpine-Borane). The reduction may be carried out in the presence of 1 mol % of chiral β-oxoaldiminatocobalt (II) complexes or in about one equivalent of a borane reducing agent such as $BH_3 \cdot THF$ (THF=tetrahydrofuran) or borane-methyl sulfide, and optionally in the presence of a catalytic amount of a single enantiomer of an oxazaborolidine derived from chiral oxazaborolidine catalyst, to obtain a compound of formula (Ig).

Examples of chiral oxazaborolidine catalysts are cis-(1R, 2S)-aminoindanol, R-diphenyl prolinol, R-methyl oxazaborolidene (derived from R-diphenyl prolinol, trimethylboroxine and methyl boronic acid), non-α-substituted (R)-indoline-2-carboxylic acid, etc.

Further, the optically pure halohydrin of formula (Ig) may be treated with at least one equivalent of a base to produce an optically pure epoxide of formula (I) without racemization. Various organic and inorganic bases such as aqueous NaOH or $K_2CO_3$ may be employed in an alcohol solvent or solvent mixture such as MeOH/TH, acetone/THF.

In the process of the present invention, the epoxide of formula (I) may be obtained without isolation of the bromohydrin of formula (Ig), preferably in the presence of a base such as piperidine, pyridine or pyrrolidine. The epoxide obtained may be purified by recrystallisation from an inert organic solvent.

The catalyst optionally used for the preparation of (Ig), for example the single enantiomer of an oxazaborolidine, may be generated in situ from R-diphenyl prolinol and diborane.

The intermediate compound of formula (If) useful in the synthesis of an oxiranyl compound of formula (I) may be prepared as shown in Scheme 3.

Scheme 3

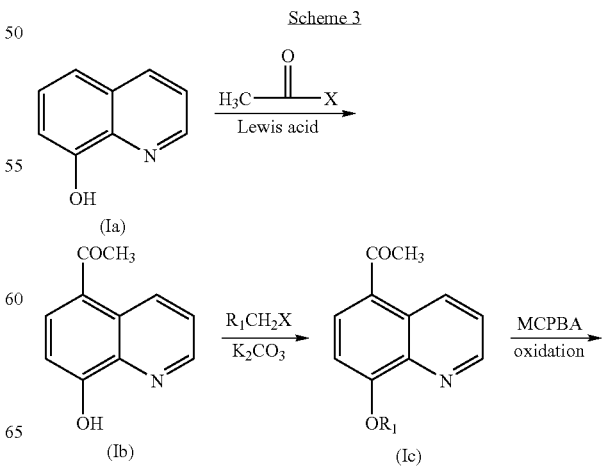

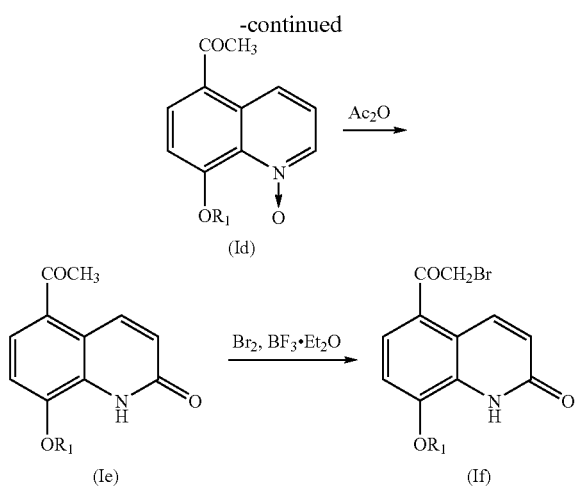

wherein compound (Ia) i.e. 8-hydroxy quinoline, may be acylated with a haloacetyl compound using a suitable Lewis acid catalyst in the presence of a suitable solvent to obtain the corresponding 5-acetyl compound of formula (Ib).

The Lewis acid catalyst used may be selected from boron trichloride, aluminum chloride, titanium tetrachloride, boron trifluoride, tin tetrachloride and zinc chloride.

The solvent used is preferably selected from a halogenated solvent, carbon disulfide and mixtures thereof, preferably dichloroethane.

In compound (Ib), the hydroxyl group may be protected using a wide variety of protecting groups such as lower alkanoyl for example a $C_1$ to $C_6$ alkanoyl, substituted or unsubstituted benzyl and substituted or unsubstituted phenyl to give compound (Ic). In the process of the present invention, benzyl bromide is a preferred reagent for protection of the hydroxy group and this results in the work up procedure being simplified by distillation, avoiding any extraction procedure.

The compound of formula (Ic) may be oxidized to the corresponding N-oxide of formula (Id) by an oxidizing agent. Suitable oxidizing agents are peracids such as peroxybenzoic acid, m-chloroperbenzoic acid, peracetic acid, peroxytrifluoroacetic acid, peroxysulfuric acid, perboric acid, performic acid, peroxymaleic acid, peroxydichloromaleic acid (for example, prepared from hydrogen peroxide and dichloromaleic anhydride), tert-butyl hydroperoxide in the presence of vanadium catalyst, dimethyl dioxirane, selenium dioxide, m-phenanthroline di-N-oxide (for example prepared from $H_2O_2$ and m-phenanthroline), nitric acid and hydrogen peroxide.

Solvents used for the process are selected from dioxane, tetrahydrofuran, diethyl ether, methanol, tert-butanol, acetic acid, sulfuric acid, water, trifluoroacetic acid, chloroform and mixtures thereof. Preferably the reaction is carried out in dichloromethane, ethyl acetate or mixture thereof.

The compound (Id) may be heated in reagents such as anhydrides including acetic anhydride and trifluoroacetic anhydride, preferably acetic anhydride, to obtain the compound of formula (Ie). The reaction may be carried out with the reagent being present in a reduced volume, for example in 2 volumes of acetic anhydride. The compound (Ie) may be isolated by crystallization using substantially low volumes of a suitable solvent such as acetic anhydride.

The compound of formula (Ie) may be brominated to obtain a bromoketone of formula (If) using a brominating agent such as N-bromosuccinimide or bromine in a solvent selected from the group consisting of tetrahydrofuran, methylene chloride, chloroform, methanol, carbon tetrachloride, or a mixture thereof; preferably dichloromethane.

The other diastereomers of carmoterol may be prepared by reacting the appropriate epoxide (I) and amine (II) following the synthetic protocol given above for (R,R)-carmoterol. Thus, the compound of formula (I) (which is depicted in the form of the R enantiomer) may be synthesised in the form of the S enantiomer and reacted with the compound of formula (I) (which is depicted in the form of the R enantiomer) in accordance with the process described above to prepare the (S,R) diastereomer of compound (III) followed by conversion to the (S,R) diastereomer of compound (IV) or (V) in accordance with the process described above, then converted to (S,R)-carmoterol in accordance with the process described above.

Alternatively, the compound of formula (II) may be synthesised in the form of the S enantiomer and reacted with the compound of formula (I) in accordance with the process described above to prepare the (R,S) diastereomer of compound (III) followed by conversion to the (R,S) diastereomer of compound (IV) or (V) in accordance with the process described above, then converted to (R,S)-carmoterol in accordance with the process described above.

Alternatively, the compound of formula (II) may be synthesised in the form of the S enantiomer and the compound of formula (I) may be synthesised in the form of the S enantiomer, and the two S enantiomers reacted in accordance with the processes described above to prepare the (S,S) diastereomer of compound (III) followed by conversion to the (S,S) diastereomer of compound (IV) or (V) in accordance with the process described above, then converted to (S,S)-carmoterol in accordance with the process described above.

EXAMPLES

The details of the invention given in the examples which are provided below for illustration only and therefore these examples should not be construed to limit the scope of the invention.

Example 1

Preparation of 5-acetyl-8-hydroxyquinoline (compound (Ib))

8-hydroxyquinoline (500 gms/3.44 moles) was dissolved in ethylene chloride (5 lits) at 25-30° C. in an inert atmosphere. To this solution was added acetyl chloride (260 ml/4.12 moles) drop wise in 2 hours. The reaction mass was stirred for 15-20 minutes. Then, aluminum chloride (1.15 Kg/8.62 moles) was added in lots in 2 hours. The reaction mass was stirred at 25-30° C. for 15-20 minutes and heated to 70° C. for 13-14 hours. After completion of reaction, the reaction mass was cooled to 25-30° C. and slowly quenched in a mixture of crushed ice (10 Kg) and conc. HCl (500 ml). The resulting slurry was stirred for 15-20 minutes. The crude 5-acetyl-8-hydroxyquinoline hydrochloride was isolated by filtration, washed with 2 liters of acetone and dried under vacuum for 1 hour. Yield: 680 gms.

A 20 liter round bottom flask was charged with wet cake (680 gms) and water (5 liters). The mixture was basified using liquor ammonia (300 ml) and stirred for 15-20 minutes. The resulting slurry was extracted with dichloromethane (3.5 liters) twice. The solution was stirred with charcoal (40 gms) and silica gel (500 gms) for 15 hours. The reaction mass was filtered on hyflo bed and washed with dichloromethane (2 liters). The clear solution was distilled under vacuum at 40°

C. The residue was stripped with diisopropyl ether (500 ml) to remove traces of dichloromethane. Residue was charged with diisopropyl ether (1 liter) and stirred. The reaction mass was warmed to 30-40° C., cooled slowly to 25-30° C., chilled to 0-5° C. and stirred for 30 minutes at the same temperature. The resulting 5-acetyl-8-hydroxyquinoline was isolated by filtration, washed with diisopropyl ether (500 ml) and dried under vacuum at 60-65° C. for 5-6 hours. Yield: 252 gms.

Example 2

Preparation of 5-acetyl-8-benzyloxyquinoline (compound (Ic); $R_1$=benzyl)

A 5 liter 4-necked flask equipped with a mechanical stirrer, thermometer, addition funnel and refluxing condenser was charged with 5-acetyl-8-hydroxyquinoline (300 gms/1.44 moles) and acetone (3 liters). To this solution was added anhydrous potassium carbonate (443 gms/1.6 moles) in 30 minutes followed by benzyl bromide (229 ml/1.92 moles) slowly in 90 minutes. The resulting slurry was heated to reflux for 12 hours. The reaction mass was filtered through hyflo bed, after completion of reaction and washed with hot ethyl acetate (300 ml). The clear filtrate was distilled out completely at 55-60° C. under high vacuum. The residue was dissolved in acetone (300 ml) and warmed to 50° C. for 5-10 minutes, cooled to 25-30° C., chilled further to 0-5° C. and stirred for 30 minutes. The resulting 5-Acetyl-8-benzyloxyquinoline was isolated by filtration and washed with 1:1 mixture of acetone and diisopropyl ether (150 ml) and dried under vacuum at 60-65° C. for 4-5 hours. Yield-202 gms.

Example 3

Preparation of 5-Acetyl-8-benzyloxyquinoline-N-oxide (compound (Id); $R_1$=benzyl)

5-Acetyl-8-benzyloxyquinoline (200 gms/0.72 moles) was dissolved in dichloromethane (4 liters) at room temperature. To this solution was added m-chloroperoxybenzoic acid (355.64 gms/1.44 moles) in 90 minutes under stiffing. The mixture was stirred at 25-30° C. for 2 hours. After completion of reaction, reaction mass was quenched with 8% sodium bicarbonate solution (3.04 liter) slowly in 30 minutes and stirred for 5-10 minutes at same temperature. The organic layer was separated and aqueous layer was extracted with dichloromethane (2.5 liters). The organic layers were combined and washed with brine solution (2.5 liters). The dichloromethane was distilled out under vacuum at 40° C. The residue was stripped with acetone (500 ml) to remove traces of dichloromethane. The residue was stirred with acetone (200 ml) and chilled to 0-5° C. for 2 hours. The resulting 5-Acetyl-8-benzyloxyquinoline-N-oxide was isolated by filtration and washed with diethyl ether (200 ml), dried under vacuum at 60-65° C. for 2-3 hours. Yield-116 gms.

Example 4

Preparation of 5-Acetyl-8-benzyloxycarbostyril (compound (Ie); $R_1$=benzyl)

5-Acetyl-8-benzyloxyquinoline-N-oxide (10 gms/0.034 moles) was charged in acetic anhydride (20 ml) at 25-30° C. The resulting slurry was heated to 40° C. and stirred for 2 hours at 40° C. After completion of reaction, the reaction mass was cooled to 25-30° C., chilled to 0-5° C. and stirred for 30 minutes at 0-5° C. The resulting 5-Acetyl-8-benzyloxycarbostyril was isolated by filtration and washed with diisopropyl ether (50 ml), dried under vacuum at 60-65° C. for 2-3 hours. Yield-7 gms.

Example 5

Preparation of 5-Bromoacetyl-8-benzyloxycarbostyril (compound (If); $R_1$=benzyl)

A dry 3 liter, 4-necked round bottom flask equipped with a mechanical stirrer, thermometer, addition funnel and refluxing condenser was charged with of 5-Acetyl-8-benzyloxycarbostyril (50 gms/0.17 moles) and dry dichloromethane (1 liter) under argon. To this solution was added boron trifluoride etharate (25.7 ml/0.204 moles). The reaction mass was heated to reflux. To this reaction mass was added slowly solution of bromine (8.4 ml/0.17 moles) in dichloromethane (100 ml) at reflux in 4 hours. The mixture was refluxed for additional 30 minutes. The mass was cooled to 30° C. and adjusted to pH 8-9 using 10% aqueous potassium carbonate solution (470 ml).

The solvent was partially distilled under vacuum at 35° C., chilled to 0-5° C. and stirred for 10-15 minutes. The resulting crude 5-Bromoacetyl-8-benzyloxycarbostyril was isolated by filtration, washed with diisopropyl ether (100 ml) and dried under vacuum at 50-55° C. for 14 hours. Yield 56.58 gms.

Purification of crude 5-Bromoacetyl-8-benzyloxycarbostyril (compound (If); $R_1$=benzyl)

The crude 5-Bromoacetyl-8-benzyloxycarbostyril (56 gms) was charged along with chloroform (280 ml) in a round bottom flask. The reaction mass was heated to reflux for 30 minutes, cooled to 25-30° C. in 2-3 hours. The reaction mass was further chilled to 0-5° C. and stirred for 30 minutes. The resulting solid was isolated by filtration, washed with chloroform (55 ml) and dried under vacuum at 55-60° C. for 4-5 hours to yield 41 gms of 5-Bromoacetyl-8-benzyloxycarbostyril.

Example 6

Preparation of 8-benzyloxy-5-[(R)-(2-bromo-1-hydroxyethyl)]-carbostyril (compound (Ig); $R_1$=benzyl)

A dry 5 liter flask equipped with a mechanical stirrer, thermometer, addition funnel and refluxing condenser was charged with 5-Bromoacetyl-8-benzyloxycarbostyril (100 gms/0.268 moles) and dry THF (1.2 liter) under argon. A solution of (R)-tetrahydro-1-methyl-3,3-diphenyl-(1H,3H)-pyrrolo[1,2-c][1,3,2]-oxazaborolidine catalyst in toluene (43 ml/0.388 moles) was added and reaction mass was chilled to 0-2° C. Then, 1M solution of borane-methyl sulfide (32.42 ml/0.3417 moles) in THF (342 ml) was added in 3 hours while maintaining temperature at 0-2° C. The reaction was stirred for another 15-20 minutes at same temperature. The reaction mass was quenched by addition of methanol (171 ml) in 15-20 minutes. The temperature of resulting solution was raised to 25-30° C. and concentrated to a volume of 500 ml under vacuum at 50° C. To this concentrate was added a mixture of water (1.45 liters) and concentrated HCl (74 ml) in 10-15 minutes. The resulting suspension was stirred for 30 minutes at 25° C. The solid 8-benzyloxy-5-[(R)-(2-bromo-1- hydroxyethyl)]-carbostyril obtained was isolated by filtration and washed with water till neutral pH, dried under vacuum at 60-65° C. for 12-14 hours. Yield-70-73 gms.

Example 7

Preparation of 8-benzyloxy-5-(R)-oxiranylcarbostyril (compound (I); $R_1$=benzyl)

A 5 liter flask equipped with a mechanical stirrer, thermometer, and refluxing condenser was charged with 8-benzyloxy-5-[(R)-(2-bromo-1-hydroxyethyl)]-carbostyril (70 gms/0.187 moles), potassium carbonate (74 gms/0.536 moles), acetone (3.5 liters) and water (35 ml). The resulting slurry was heated to reflux and maintained for 2½ hours. After completion of reaction, the hot mass was filtered on hylo bed to remove inorganics. The residue was slurried in dichloromethane (200 ml) and filtered on hyflo bed. The filtrates were combined together and concentrated under vacuum completely. The residue was dissolved in dichloromethane (500 ml) and filtered on hyflo bed to remove traces of insolubles and washed with dichloromethane (100 ml). The clear filtrate was distilled completely to obtain residue. The residue was charged with methanol (70 ml), stirred and heated to 50° C. for 30 minutes. The slurry obtained was cooled to 25-30° C., chilled to 0-5° C., stirred for 1 hour. The resulting solid was isolated by filtration, washed with methanol (30 ml), followed by diisopropylether (100 ml) and dried under vacuum at 60-65° C. for 10-12 hours to yield 40-41 gms of 8-benzyloxy-5-(R)-oxiranylcarbostyril.

Example 8

Preparation of 8-benzyloxy-5-(R)-oxiranylcarbostyril from 5-Bromoacetyl-8-benzyloxycarbostyril (compound (I); $R_1$=benzyl)

A dry 250 ml flask equipped with a mechanical stirrer, thermometer, addition funnel and refluxing condenser was charged with of 5-Bromoacetyl-8-benzyloxycarbostyril (5 gms/0.0134 moles) along with dry THF (60 ml) under argon. A solution of (R)-tetrahydro-1-methyl-3,3-diphenyl-(1H,3H)-pyrrolo[1,2-c][1,3,2]-oxazaborolidine catalyst (2.15 ml/0.002 moles) in toluene was added and reaction mass was cooled to 0-2° C. Then, 1 molar solution of boron dimethyl sulfide (1.62 ml/0.017 moles) in THF (17 ml) was added in 45 minutes while maintaining temperature of 0-2° C. The reaction was stirred further for 1 hour at same temperature and then quenched by adding solution of piperidine (8.5 ml/0.0861 moles) in water (80 ml) in 30 minutes. The reaction mass was stirred at 0-2° C. for 30 minutes. After completion of reaction, reaction mass was brought to 20-22° C. and extracted with dichloromethane (50 ml) thrice. The combined dichloromethane extracts were washed with water (100 ml) thrice. The organic layer was distilled out completely under vacuum at 30° C. To the resulting residue was added methanol (12 ml), and warmed to 50° C. for 5-10 minutes. The slurry obtained was cooled to 25-30° C. and stirred for 30 minutes. The resulting 8-benzyloxy-5-(R)-oxiranylcarbostyril was isolated by filtration and washed with methanol (10 ml), followed by diisopropylether (30 ml), dried under vacuum at 60-65° C. for 10-12 hours. Yield-1.2 gms.

Example 9

Preparation of 8-benzyloxy-5-{((1R)-1-hydroxy-2-[N-(1R)-2-(p-methoxyphenyl)-1-methylethyl)amino] ethyl}carbostyril oxalate (oxalate salt of compound (IV); $R_1$=benzyl)

(Step-1)-Preparation of (R)—N-trimethylsilyl[2-(p-methoxyphenyl)-1-methylethyl)]amine (compound (II); $R_2$=trimethylsilyl)

(R)—N-[2-(p-methoxyphenyl)-1-methylethyl)]amine hydrochloride (22.6 gms/0.112 moles) was dissolved in dichloromethane (226 ml), water (452 ml) and basified with liquor ammonia (22 ml). The organic layer was separated, dried on sodium sulfate and concentrated under vacuum at 30° C. The residue obtained was dissolved in diglyme (60 ml) under argon. Then, added hexamethyldisilazane (25.6 ml/0.121 moles) at 25° C. The reaction mass was heated to 110° C. for 1 hour and cooled to 30° C. to get a clear solution.

(a) Preparation of 8-benzyloxy-5-{((1R)-1-hydroxy-2-[N-(1R)-2-(p-methoxyphenyl)-1-methylethyl) amino]ethyl}carbostyril oxalate (compound (V); $R_1$=benzyl; $A^-$=oxalate)

A dry 250 ml flask equipped with a mechanical stirrer, thermometer, addition funnel and refluxing condenser was charged with of 8-benzyloxy-5-(R)-oxiranylcarbostyril (30 gms/0.102 moles) and diglyme (60 ml) under argon. The reaction mass was heated to 100° C. and charged with solution prepared in Step-1, slowly in 5 hours. The clear solution obtained was further heated at 100° C. for 25 hours. After completion of reaction, reaction mass was cooled to 80° C. Then, solution of oxalic acid dihydrate (25.6 gms/0.203 moles) in ethanol (150 ml) charged to reaction mass at 80° C. slowly. The reaction mass was stirred for 30 minutes at 80° C., cooled to 25° C. gradually and stirred for 16 hours. The resulting solid was isolated by filtration, washed with ethanol (100 ml), and dried under vacuum at 60-65° C. for 10-12 hours to yield 50 gms of 8-benzyloxy-5-{((1R)-1-hydroxy-2-[N-(1R)-2-(p-methoxyphenyl)-1-methyl ethyl)amino] ethyl}carbostyril oxalate.

Similarly, using the procedure described in Example 9a, the following compounds were prepared.
(b) 8-benzyloxy-5-{((1R)-1-hydroxy-2-[N-(1R)-2-(p-methoxyphenyl)-1-methylethyl amino]ethyl}carbostyril fumarate.
(c) 8-benzyloxy-5-{((1R)-1-hydroxy-2-[N-(1R)-2-(p-methoxyphenyl)-1-methylethyl amino]ethyl}carbostyril tartrate.
(d) 8-benzyloxy-5-{((1R)-1-hydroxy-2-[N-(1R)-2-(p-methoxyphenyl)-1-methylethyl amino]ethyl}carbostyril benzoate.
(e) 8-benzyloxy-5-{((1R)-1-hydroxy-2-[N-(1R)-2-(p-methoxyphenyl)-1-methylethyl amino]ethyl}carbostyril salicylate.
(f) 8-benzyloxy-5-{((1R)-1-hydroxy-2-[N-(1R)-2-(p-methoxyphenyl)-1-methylethyl amino]ethyl}carbostyril di-p-toluoyl D-tartrate.
(g) 8-benzyloxy-5-{((1R)-1-hydroxy-2-[N-(1R)-2-(p-methoxyphenyl)-1-methylethyl amino]ethyl}carbostyril di-benzoyl D-tartrate.
(h) 8-benzyloxy-5-{((1R)-1-hydroxy-2-[N-(1R)-2-(p-methoxyphenyl)-1-methylethyl amino]ethyl}carbostyril di-pivaloyl D-tartrate.

(i) 8-benzyloxy-5-{((1R)-1-hydroxy-2-[N-(1R)-2-(p-methoxyphenyl)-1-methylethyl amino]ethyl}carbostyril succinate.
(j) 8-benzyloxy-5-{((1R)-1-hydroxy-2-[N-(1R)-2-(p-methoxyphenyl)-1-methylethyl amino]ethyl}carbostyril glutamate.
(k) 8-benzyloxy-5-{((1R)-1-hydroxy-2-[N-(1R)-2-(p-methoxyphenyl)-1-methylethyl amino]ethyl}carbostyril ethylenediaminetetraacetate.
(l) 8-benzyloxy-5-{((1R)-1-hydroxy-2-[N-(1R)-2-(p-methoxyphenyl)-1-methylethyl amino]ethyl}carbostyril maleate.
(m) 8-benzyloxy-5-{((1R)-1-hydroxy-2-[N-(1R)-2-(p-methoxyphenyl)-1-methylethyl amino]ethyl}carbostyril mandelate.
(n) 8-benzyloxy-5-{((1R)-1-hydroxy-2-[N-(1R)-2-(p-methoxyphenyl)-1-methylethyl amino]ethyl}carbostyril malonate.
(o) 8-benzyloxy-5-{((1R)-1-hydroxy-2-[N-(1R)-2-(p-methoxyphenyl)-1-methylethyl amino]ethyl}carbostyril acetate.
(p) 8-benzyloxy-5-{((1R)-1-hydroxy-2-[N-(1R)-2-(p-methoxyphenyl)-1-methylethyl amino]ethyl}carbostyril anthranilate.
(q) 8-benzyloxy-5-{((1R)-1-hydroxy-2-[N-(1R)-2-(p-methoxyphenyl)-1-methylethyl amino]ethyl}carbostyril maleate.
(r) 8-benzyloxy-5-{((1R)-1-hydroxy-2-[N-(1R)-2-(p-methoxyphenyl)-1-methylethyl amino]ethyl}carbostyril nicotinate.
(s) 8-benzyloxy-5-{((1R)-1-hydroxy-2-[N-(1R)-2-(p-methoxyphenyl)-1-methylethyl amino]ethyl}carbostyril furoate.

Example 10

Preparation of 8-benzyloxy-5-{((1R)-1-hydroxy-2-[N-(1R)-2-(p-methoxyphenyl)-1-methylethyl)amino]ethyl}carbostyril oxalate (compound (V); $R_1$=benzyl, $A^-$=oxalate)

(Step-1)-Preparation of (+)-(R)—N-[2-(p-methoxyphenyl)-1-methylethyl)]amine (R)—N-[2-(p-methoxyphenyl)-1-methylethyl)]amine hydrochloride (22.6 gms/0.112 moles) was dissolved in dichloromethane (226 ml), water (452 ml) and basified with liquor ammonia (22 ml). The organic layer was separated, dried on sodium sulfate and concentrated under vacuum at 30° C. The residue obtained was dissolved in HMPA (60 ml) under argon.

(a) Preparation of 8-benzyloxy-5-{((1R)-1-hydroxy-2-[N-(1R)-2-(p-methoxyphenyl)-1-methylethyl)amino]ethyl}carbostyril oxalate A dry 250 ml flask equipped with a mechanical stirrer, thermometer, addition funnel and refluxing condenser was charged with of 8-benzyloxy-5-(R)-oxiranylcarbostyril (30 gms/0.102 moles) and hexamethylphosphoramide (60 ml) under argon. The reaction mass was stirred and charged with solution prepared in Step-1 at 25° C. The clear solution obtained was further heated at 80° C. for 45 hours. After completion of reaction, the reaction mass was cooled to 80° C. Then, a solution of oxalic acid dihydrate (25.6 gms/0.203 moles) in ethanol (150 ml) was charged to the reaction mass at 80° C. slowly. The reaction mass was stirred for 30 minutes at 80° C., cooled to 25° C. gradually and stirred for 16 hours. The resulting solid was isolated by filtration, washed with ethanol (100 ml), and dried under vacuum at 60-65° C. for 10-12 hours to yield 30 gms of 8-benzyloxy-5-{((1R)-1-hydroxy-2-[N-(1R)-2-(p-methoxyphenyl)-1-methylethyl)amino]ethyl}carbostyril oxalate.

Example 11

Preparation of 8-benzyloxy-5-{((1R)-1-hydroxy-2-[N-(1R)-2-(p-methoxyphenyl)-1-methylethyl)amino]ethyl}carbostyril oxalate (compound (V); $R_1$=benzyl, $A^-$=oxalate)

(Step-1) Preparation of (R)—N-Trimethylsilyl[2-(p-methoxyphenyl)-1-methylethyl)]amine (compound II; $R_2$=trimethylsilyl)

(R)—N-[2-(p-methoxyphenyl)-1-methylethyl)]amine hydrochloride (7.55 gms/0.0375 moles) dissolved in dichloromethane (75 ml) water (150 ml and basified with liquor ammonia (8 ml). The organic layer was separated, dried on sodium sulfate and concentrated under vacuum at 30° C. The residue obtained was dissolved in HMPA (10 ml) under argon. Then, added hexamethyldisilazane (9 ml/0.0409 moles) at 25° C. The reaction mass was heated to 80° C. for 1 hour and cooled to 30° C. to obtain a clear solution.

(a) Preparation of 8-benzyloxy-5-{((1R)-1-hydroxy-2-[N-(1R)-2-(p-methoxyphenyl)-1-methylethyl)amino]ethyl}carbostyril oxalate (compound (V); R1=benzyl; $A^-$=oxalate)

A dry 250 ml flask equipped with a mechanical stirrer, thermometer, addition funnel and refluxing condenser was charged with of 8-benzyloxy-5-(R)-oxiranylcarbostyril (10 g 0.102 moles) and HMPA (20 ml) under argon. The reaction mass was heated to 80° C. and charged with solution prepared in Step-1, slowly in 5 hours. The clear solution obtained was further heated at 80° C. for 45 hours. After completion of reaction, reaction mass was cooled to 50° C. Then, a solution of oxalic acid dihydrate (6 gms/0.0477 moles) in ethanol (100 ml) was charged to the reaction mass at 50° C. slowly. The reaction mass was stirred for 30 minutes at 50° C., cooled to 25° C. gradually and stirred for 16 hours. The resulting solid was isolated by filtration, washed with ethanol (100 ml), and dried under vacuum at 60-65° C. for 10-12 hours to yield 10 gms of 8-benzyloxy-5-{((1R)-1-hydroxy-2-[N-(1R)-2-(p-methoxyphenyl)-1-methylethyl)amino]ethyl}carbostyril oxalate.

Example 12

Preparation of 8-benzyloxy-5-{((1R)-1-hydroxy-2-[N-(1R)-2-(p-methoxyphenyl)-1-methylethyl)amino]ethyl}carbostyril hydrochloride (compound (V); $R_1$=benzyl; $A^-$=chloride)

8-benzyloxy-5-{((1R)-1-hydroxy-2-[N-(1R)-2-(p-methoxyphenyl)-1-methylethyl)amino]ethyl}carbostyril oxalate (50 gms/0.0912 moles) prepared as per example 9a, was charged in round bottom flask along with dichloromethane (100 ml). The reaction mass was basified with 10% sodium hydroxide (50 ml). The organic layer was separated and washed with water (100 ml) thrice. The organic layer was dried on sodium sulfate, concentrated under vacuum completely at 35° C. The residue obtained was dissolved in isopropanol (450 ml) and IPA-HCl (50 ml) was charged dropwise to adjust the pH 3 to 4. The reaction mass was heated to reflux to obtain thick slurry. Then, while maintaining reflux, water (50 ml) was added drop wise in 30 minutes. The clear solution obtained was cooled to 25° C. in 14 hours and further chilled to 10° C. for 1 hour. The resulting 8-benzyloxy-5-{((1R)-1-hydroxy-2-[N-(1R)-2-(p-methoxyphenyl)-1-methylethyl)amino]ethyl}carbostyril hydrochloride was isolated by filtration and washed with isopropanol (100 ml), dried under vacuum at 60-65° C. for 10-12 hours. Yield-40 gms.

The title compound was similarly prepared using the process of Example 10 but using products from Examples 9b to 9s as starting material.

Example 13

Preparation of 8-benzyloxy-5-{((1R)-1-hydroxy-2-[N-(1R)-2-(p-methoxyphenyl)-1-methylethyl)amino]ethyl}carbostyril hydrochloride (compound (V); $R_1$=benzyl; $A^-$=chloride)

A mixture of methanol (500 ml), THF (500 ml), 8-benzyloxy-5-(R)-oxiranylcarbostyril (83 gms/0.283 moles), (R)-(+)-N-(1-phenylethyl)-N-[1-(p-methoxyphenyl)-2-propyl)]amine hydrochloride (83 gms/0.271 moles) and powdered potassium carbonate (37.4 gms/0.271 moles) were charged in a dry flask under argon at RT under stirring. The reaction mass was stirred at 25-30° C. for 1 hour and concentrated under vacuum at 30-35° C. The slurry obtained was stirred with toluene (1 liter) for 30 minutes. The reaction mass was then charged with water (1 liter) and stirred for 30 minutes at same temperature. The organic layer was separated and aqueous layer was back extracted with toluene (200 ml). The organic layers were combined together, washed with water until neutral pH (4×500 ml), dried on sodium sulfate and concentrated under vacuum below 35° C. to remove solvent. The residue was stripped with heptane (500 ml) thrice to remove traces of toluene. The residue was heated to 140° C. slowly under stirring in an inert atmosphere. The heating was continued for 30-35 hours. The reaction mass was cooled to 35° C. and stirred with dichloromethane (1 liter) and continued to stir for 30 minutes more at the same temperature. The mass was cooled to RT. The solution was stirred with charcoal (20 gms) and silica gel (40 gms) for 30 minutes at room temperature, filtered on hyflo bed and washed with dichloromethane (100 ml). The clear filtrate was acidified with IPA-HCl (100 ml) and distilled completely under vacuum at 50° C. The residue obtained was stripped with diisopropyl ether (100 ml) thrice to remove traces of dichloromethane and IPA. The residue was charged with diisopropyl ether (500 ml) at 50° C. and stirred for 30 minutes. The slurry obtained was brought to 25-30° C. and further stirred for 30 minutes at same temperature. The solid obtained was isolated by filtration and washed with diisopropyl ether (200 ml), dried under vacuum at 40-45° C. for 4-5 hours. To yield 105 gms of 8-benzyloxy-5-{((1R)-1-hydroxy-2-[N-(1R)-2-(p-methoxyphenyl)-1-methylethyl)amino]ethyl}carbostyril hydrochloride.

Example 14

Preparation of 8-hydroxy-5-{((1R)-1-hydroxy-2-[N-(1R)-2-(p-methoxyphenyl)-1-methylethyl)amino]ethyl}carbostyril hydrochloride (R,R-carmoterol hydrochloride)

A mixture of 8-benzyloxy-5-{((1R)-1-hydroxy-2-[N-(1R)-2-(p-methoxyphenyl)-1-methylethyl)amino]ethyl}carbostyril hydrochloride (25 gms/0.050 moles), methanol (250 ml) and slurry of 10% Pd/C catalyst (2.5 gms) in water (25 ml) ware charged in a hydrogenator at 25° C. The reaction was hydrogenated at 25° C. by applying 40-45 psi for 1 hour. After completion of reaction, the reaction mass was filtered on hyflo bed. The hyflo bed was washed with methanol (100 ml). The clear filtrate was stirred with 2% charcoal for 30 minutes at 25-30° C., filtered on hyflo bed and washed with methanol (100 ml). The clear filtrate was distilled completely under vacuum at 50° C. The residue obtained was stripped with ethanol (100 ml) thrice to remove traces of methanol. To the residue was charged ethanol (125 ml). The reaction mass was heated to reflux for 1 hour and then cooled to 25° C. slowly in 6 hours. The resulting solid was isolated by filtration and washed with ethanol (50 ml), dried under vacuum at 50-55° C. for 12-14 hours to yield-11 gms of 8-hydroxy-5-{((1R)-1-hydroxy-2-[N-(1R)-2-(p-methoxyphenyl)-1-methylethyl)amino]ethyl}carbostyril hydrochloride i.e. R,R-carmoterol hydrochloride.

Example 15

Preparation of (+)-(R)—N-(1-phenylethyl)-N-[1-(p-methoxyphenyl)-2-propyl)]amine hydrochloride 4-methoxy phenyl acetone (400 gms/2.439 moles), R(+)-phenyl ethyl amine (300 gms/2.479 moles), RaneyNickel (100 gms) and methanol (2.4 liters) were charged in a hydrogenator. Reaction mass was hydrogenated at 70° C. by applying hydrogen pressure of 10 Kg/cm$^2$ for 25 hours. After completion of reaction, reaction mass was cooled to 25-30° C. and filtered on hyflo bed and washed with methanol (400 ml). The pH was adjusted to 1-2 using solution of HCl in IPA (1.1 liter). The clear filtrate was distilled out under vacuum at 65° C. to volume of 500 ml. The residue was stripped with ethyl acetate (500 ml) thrice to remove traces of methanol. The residue was charged with ethyl acetate (2.0 liters) at 65° C. and stirred for 30 minutes. The slurry obtained was brought to 25-30° C., chilled to 0-5° C. and further stirred for 30 minutes. The resulting (+)-(R)—N-(1-Phenylethyl)-N-[1-(p-methoxyphenyl)-2-propyl)]amine hydrochloride was isolated by filtration and washed with ethyl acetate (200 ml), dried under vacuum at 60-65° C. for 12-14 hours. Yield-470 gms.

Example 16

Preparation of (+)-(R)—N-[2-(p-methoxyphenyl)-1-methylethyl)]amine hydrochloride (hydrochloride salt of compound (II))

(R)-(+)-N-(1-Phenylethyl)-N-[1-(p-methoxyphenyl)-2-propyl)]amine hydrochloride (464 gms/1.591 moles), slurry of 10% Pd/C (93 gms) in methanol (4.64 liters) were charged in a hydrogenator. Hydrogenated reaction mass at 50° C. for 8-10 hours by applying 5 Kg hydrogen pressure. The reaction mass was cooled to room temperature, filtered on hyflo bed to remove catalyst and washed with methanol (500 ml). The filtrates were combined and acidified to pH 1-2 using IPA-HCl (750 ml). The clear filtrate was distilled out completely under vacuum at 50° C. The residue was stripped with acetone (500 ml) twice to remove traces of methanol. The residue was charged with ethyl acetate (2.0 liters) at 65° C. and stirred for 30 minutes. The residue was slurried in acetone (1.6 liters), cooled to 25-30° C. The resulting (+)-(R)—N-[2-(p-methoxyphenyl)-1-methylethyl)]amine hydrochloride was isolated by filtration and washed with acetone (400 ml), dried under vacuum at 50-55° C. for 2-4 hours. Yield-285 gms.

Example 17

Preparation of 8-hydroxy-5-{((1R)-1-hydroxymethyl-2-[N-(1R)-2-(p-methoxyphenyl)-1-methylethyl)amino]ethyl}carbostyril oxalate (Regio isomer)

(a) A dry 250 ml flask equipped with a mechanical stirrer, thermometer, addition funnel and refluxing condenser was charged with (R)—N-[2-(p-methoxyphenyl)-1-methylethyl)]amine hydrochloride (3.78 gms/0.0187 moles), dichloromethane (50 ml), water (100 ml) and basified with liquor ammonia (5 ml). The organic layer was separated, dried on sodium sulfate and concentrated under vacuum at 30° C. The residue obtained was dissolved in diglyme (10 ml) under argon. Then, added hexamethyldisilazane (4.275 ml/0.02 moles) at 25° C. The reaction mass was heated to 110° C. for 1 hour and cooled to 75° C. The reaction mass was charged with solution of 8-benzyloxy-5-(R)-oxiranylcarbostyril (5 gms/0.017 moles) in diglyme (10 ml) followed by methane sulfonic acid (0.5 ml). The reaction mass was slowly heated to 100° C. The clear solution obtained was further heated at 100° C. for 25 hours. After completion of reaction, reaction mass was cooled to 80° C. Then, solution of oxalic acid dihydrate (4.15 gms/0.0329 moles) in ethanol (25 ml) charged slowly to reaction mass at 80° C. The reaction mass was stirred for 30 minutes, cooled to 25° C. gradually and stirred for 16 hours. The resulting solid was isolated by filtration and washed with ethanol (15 ml), dried under vacuum at 60-65° C. for 10-12 hours to yield 5.0 gms of 8-benzyloxy-5-{((1R)-1-hydroxymethyl-2-[N-(1R)-2-(p-methoxyphenyl)-1-methylethyl)amino]ethyl}carbostyril oxalate.

(b) The oxalate salt obtained in the Example 15a was then hydrogenated using the process of Example 12, to yield 3.0 gms of 8-hydroxy-5-{((1R)-1-hydroxymethyl-2-[N-(1R)-2-(p-methoxyphenyl)-1-methylethyl)amino]ethyl}carbostyril oxalate.

Example 18

Preparation of 8-benzyloxy-5-{((1R)-1-hydroxy-2-[N-(1R)-2-(p-methoxyphenyl)-1-methylethyl)amino]ethyl}carbostyril (compound (IV); $R_1$=benzyl)

(R)—N-[2-(p-methoxyphenyl)-1-methylethyl)]amine hydrochloride (7.56 gms/0.0375 moles) was dissolved in dichloromethane (200 ml), water (400 ml) and basified with sodium hydroxide (1.6 gms/0.04 moles). The organic layer was separated, dried on sodium sulfate and concentrated under vacuum at 30° C. The residue obtained was dissolved in IPA (200 ml) under argon. Then, added 8-benzyloxy-5-(R)-oxiranylcarbostyril (10 gms/0.0341 moles). The reaction mass was slowly heated to 85-90° C. for 20-25 hours, cooled to 30° C., filtered on hyflo bed, washed bed with IPA (50 ml). The clear filtrate was concentrated under vacuum at 50° C. The residue was stripped with diisopropyl ether (100 ml) twice to remove traces of IPA. The residue was charged with diisopropyl ether (100 ml) at 50° C., stirred for 30 minutes and cooled to 30° C. The resulting (+) (R)—N-[2-(p-methoxyphenyl)-1-methylethyl)]amine was isolated by filtration and washed with diisopropyl ether (50 ml), dried under vacuum at 35-40° C. for 2-4 hours. Yield-7.2 gms.

Example 19

Preparation of 8-benzyloxy-5-{((1R)-1-hydroxy-2-[N-(1R)-2-(p-methoxyphenyl)-1-methylethyl)amino]ethyl}carbostyril hydrochloride (compound (V); $R_1$=benzyl; $A^-$=chloride) without isolation of base 8-benzyloxy-5-{((1R)-1-hydroxy-2-[N-(1R)-2-(p-methoxyphenyl)-1-methylethyl)amino]ethyl}carbostyril oxalate (1 gm/0.00182 moles) prepared as per example 9a, was charged in round bottom flask along with isopropanol (10 ml). The reaction mass was heated to 80° C. and charged with IPA-HCl (1 ml) dropwise to pH 3 to 4. The reaction mass was heated to reflux for 5-10 minutes. The clear solution obtained was cooled to 25° C., stirred for 12 to 14 hours at same temperature and further chilled to 10° C. for 1 hour. The resulting 8-benzyloxy-5-{((1R)-1-hydroxy-2-[N-(1R)-2-(p-methoxyphenyl)-1-methylethyl)amino]ethyl}carbostyril hydrochloride was isolated by filtration and washed with isopropanol (5 ml), dried under vacuum at 60-65° C. for 5-6 hours. Yield-0.6 gms.

The (R,R)-carmoterol or other diastereomers of carmoterol as described above may be formulated into pharmaceutical compositions suitable for treating conditions requiring a bronchodilating effect, such as asthma and chronic obstructive pulmonary disease (COPD). Such compositions are well known in the prior art. For example, the carmoterol may be administered as a liquid (aqueous or hydroalcoholic) formulation through a nebuliser, as a dry powder by means of a Dry Powder Inhaler (DPIs) or in a halogenated hydrocarbon propellant which requires a suitable pressurized metered-dose inhaler (pMDIs) releasing a metered dose of medicine upon each actuation.

The carmoterol may be in the form of a liquid, propellant-free pharmaceutical formulation, as disclosed in US 2007/0065366.

It will be appreciated that the invention may be modified within the scope of the appended claims.

The invention claimed is:

1. A process for preparing the (R,R)—, (S,S)—, (R,S)— or (S,R)-diastereomer of a compound of formula (III)

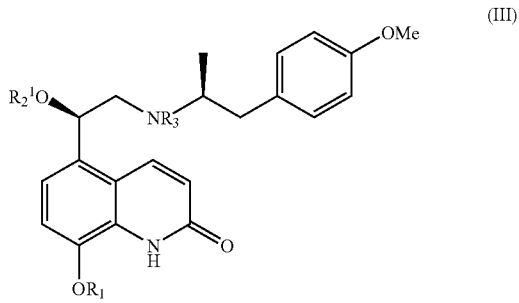

comprising condensing the R or S enantiomer of an oxiranyl compound of formula (I)

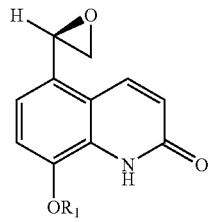

with the R or S enantiomer of an amine of formula (II) or a salt thereof

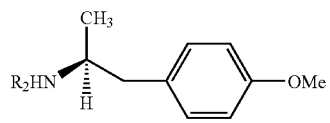

wherein: $R_1$ is a group selected from alkyl, aryl, allyl, alkoxy, cycloalkyl, heterocyclic, alkenyl, benzocycloalkyl, aralkyl, haloarylalkyl, heteroaralkyl, haloalkyl, alkoxyaralkyl, and optionally substituted silyl and benzyl; and either (a) $R_2$ and $R_2'$ are trialkylsilyl and $R_3$ is hydrogen; (b) $R_2$ and $R_3$ are trialkylsilyl and $R_2'$ is hydrogen; (c) $R_2$ and $R_2'$ are diarylalkylsilyl and $R_3$ is hydrogen; or (d) $R_2$ and $R_3$ are diarylalkylsilyl and $R_2'$ is hydrogen.

2. The process according to claim 1, wherein the process is carried out in HMPA solvent.

3. The process according to claim 1, wherein $R_1$ is benzyl.

4. The process according to claim 1, wherein the process further comprises converting the (R,R)—, (S,S)—, (R,S)—or (S,R)-diastereomer of compound of formula (III) to the corresponding (R,R)—, (S,S)—, (R,S)—or (S,R)-diastereomer of carmoterol.

5. The process according to claim 4, wherein the process further comprises converting the (R,R)-diastereomer of compound of formula (III) to the (R,R)-diastereomer of carmoterol.

6. The process according to claim 1, wherein the process further comprises hydrolyzing the (R,R)—, (S,S)—, (R,S)—or (S,R)-diastereomer of the compound of formula (III) in the presence of an acid to obtain the corresponding (R,R)—, (S,S)—, (R,S)—or (S,R)-diastereomer of a compound of formula (IV)

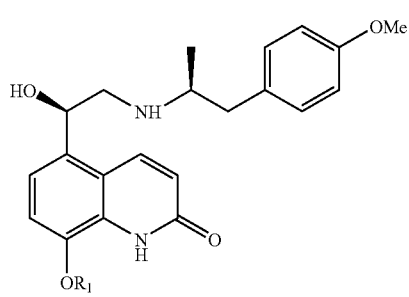

wherein $R_1$ is a group selected from alkyl, aryl, allyl, alkoxy, cycloalkyl, heterocyclic, alkenyl, benzocycloalkyl, aralkyl, haloarylalkyl, he teroaralkyl, haloalkyl, alkoxyaralkyl, and optionally substituted silyl and benzyl.

7. The process according to claim 6, wherein the acid is a carboxylic acid or a mineral acid, preferably selected from the group consisting of benzoic acid, oxalic acid, maleic acid, succinic acid, fumaric acid, tartaric acid, hydrochloric acid, salicylic acid, di-p-toluyl-D-tartaric acid, di-benzoyl-D-tartaric acid, di-pivaloyl-D-tartaric acid, glutamic acid, ethylenediaminetetraacetic acid, mandelic acid, malonic acid, acetic acid, anthranilic acid, nicotinic acid and furoic acid.

8. The process according to claim 6, wherein the condensation and hydrolyzation steps are carried out without isolation of the compound (III).

9. The process according to claim 6, wherein compound (IV) is produced in the form of its acid addition salt as a compound of formula (V)

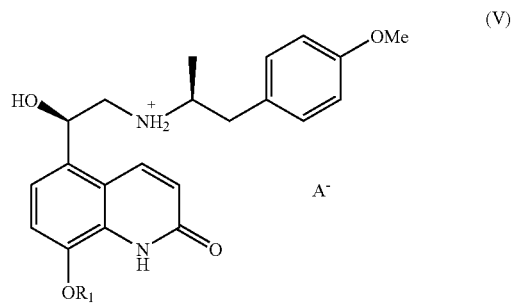

wherein $R_1$ is a group selected from alkyl, aryl, allyl, alkoxy, cycloalkyl, heterocyclic, alkenyl, benzocycloalkyl, aralkyl, haloarylMkyl, heteroaralkyl, haloalkyl, alkoxyaralkyl, and optionally substituted silyl and benzyl and $A^-$ is an anion, preferably selected from the group consisting of oxalate, fumarate, tartrate, benzoate, salicylate, di-p-toluyl D-tartrate, di-benzoyl D-tartrate, di-pivaloyl D-tartrate, succinate, glutamate, ethylenediaminetetraacetate, maleate, mandelate, malonate, acetate, anthranilate, nicotinate and furoate.

10. The process according to claim 9, wherein the compound of formula (IV) or (V) is isolated by crystallization.

11. The process according to claim 6, wherein the process further comprises converting the (R,R)—, (S,S)—, (R,S)—or (S,R)-diastereomer of the compound of formula (IV) or (V) to the (R,R)—, (S,S)—, (R,S)—or (S,R)-diastereomer of carmoterol.

12. The process according to claim 11, wherein the condensation, hydrolyzation and deprotection steps are carried out without isolation of the compounds (III) and (IV) or (V).

13. The process according to claim 4, wherein the carmoterol is converted to a pharmaceutically acceptable salt thereof.

14. The process according to claim 1 wherein the compound of formula (II)

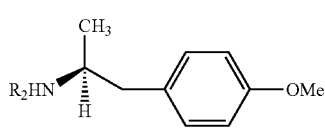

is prepared by a process comprising converting (R)—N-(2-(p-methoxyphenyl)-1-methylethyl)amine to the compound of formula (II).

15. The process according to claim 14, wherein the conversion comprises reacting (R)—N-(2-(p-methoxyphenyl)-1-methylethyl)amine with a silylating agent.

16. The process according to claim 13, wherein the pharmaceutically acceptable salt is hydrochloride salt.

17. The process according to claim 15, wherein the silylating agent is hexamethyldisilazane or hexaethyldisilazane.

* * * * *